(12) United States Patent
Sato et al.

(10) Patent No.: US 7,989,523 B2
(45) Date of Patent: Aug. 2, 2011

(54) ALICYCLIC DIEPOXY COMPOUND, EPOXY RESIN COMPOSITION COMPRISING THE SAME, AND CURED ARTICLE THEREFROM

(75) Inventors: Atsushi Sato, Ohtake (JP); Hideyuki Takai, Ohtake (JP); Hisashi Maeshima, Ohtake (JP); Kyuhei Kitao, Ohtake (JP)

(73) Assignee: Daicel Chemical Industries, Ltd., Osaka-Shi (JP)

( * ) Notice: Subject to any disclaimer, the term of this patent is extended or adjusted under 35 U.S.C. 154(b) by 243 days.

(21) Appl. No.: 12/305,906

(22) PCT Filed: Jun. 29, 2007

(86) PCT No.: PCT/JP2007/063109
§ 371 (c)(1),
(2), (4) Date: Dec. 19, 2008

(87) PCT Pub. No.: WO2008/004504
PCT Pub. Date: Jan. 10, 2008

(65) Prior Publication Data
US 2010/0249341 A1     Sep. 30, 2010

(30) Foreign Application Priority Data

Jun. 7, 2006  (JP) ................................. 2006-187167
Apr. 27, 2007  (JP) ................................. 2007-118344

(51) Int. Cl.
C08G 59/24   (2006.01)
C08G 59/22   (2006.01)
C08G 59/20   (2006.01)
C08L 63/00   (2006.01)
C08L 63/08   (2006.01)
B32B 27/38   (2006.01)

(52) U.S. Cl. ......... 523/427; 523/400; 528/219; 528/271
(58) Field of Classification Search ................. 523/400, 523/427; 528/271, 219
See application file for complete search history.

(56) References Cited

U.S. PATENT DOCUMENTS

| | | | | |
|---|---|---|---|---|
| 7,781,543 B2 * | 8/2010 | Maeshima et al. | ............ | 525/533 |
| 2006/0009547 A1 | 1/2006 | Maeshima et al. | | |
| 2010/0216912 A1 * | 8/2010 | Oka | ............... | 523/466 |

FOREIGN PATENT DOCUMENTS

| | | | |
|---|---|---|---|
| JP | 2000-169399 A | * | 6/2000 |
| JP | 2004-099467 A | | 4/2004 |
| JP | 2004-204228 A | | 7/2004 |
| JP | 2005-097274 A | | 4/2005 |
| WO | WO-2004/035558 A1 | | 4/2004 |

OTHER PUBLICATIONS

Machine translation of JP 2000-169399 A, provided by the JPO website (no date).*
Extended European Search Report issued Aug. 16, 2010, in counterpart EP 07767896.9 (including Supplementary European Search Report and European Search Opinion).

* cited by examiner

*Primary Examiner* — Michael J Feely
(74) *Attorney, Agent, or Firm* — Birch, Stewart, Kolasch & Birch, LLP

(57) ABSTRACT

Disclosed is an alicyclic diepoxy compound which gives a cured article suffering from no deterioration in properties even when used in hot and humid surroundings or used under such conditions as to give a strong acid, which is highly reactive upon curing, and which gives a cured article superior typically in thermal stability. Specifically, the alicyclic diepoxy compound includes a 3,4,3',4'-diepoxybicyclohexyl compound represented by following Formula (1):

[Chemical Formula 1]

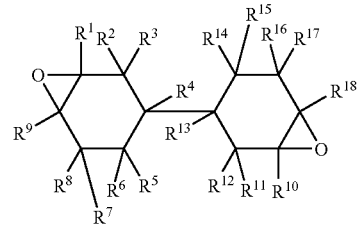

(1)

wherein R1 to R18 each represent a hydrogen atom, a halogen atom, a hydrocarbon group which may have an oxygen atom or a halogen atom, or a substituted or unsubstituted alkoxy group, in which the alicyclic diepoxy compound contains isomers of the 3,4,3',4'-diepoxybicyclohexyl compound in a content of less than 20% based on the total of the 3,4,3',4'-diepoxybicyclohexyl compound and the isomers thereof in terms of peak area ratio as determined by gas chromatography.

9 Claims, 15 Drawing Sheets

| PKNO | TIME | AREA | MK | IDNO | CONC | NAME |
|---|---|---|---|---|---|---|
| 1 | 2.717 | 2304764 | S E | | 95.3168 | |
| 2 | 2.828 | 318 | T | | 0.0128 | |
| 3 | 2.936 | 150 | T | | 0.0062 | |
| 4 | 19.13 | 2262 | V | | 0.0935 | |
| 5 | 19.313 | 1715 | V | | 0.0709 | |
| 6 | 19.582 | 5702 | V | | 0.2358 | |
| 7 | 19.816 | 28514 | V | | 1.1793 | |
| 8 | 19.984 | 74587 | V | | 3.0846 | |
| TOTAL | | 2418002 | | | 100 | |

| PKNO | TIME | AREA | MK | IDNO | CONC | NAME |
|---|---|---|---|---|---|---|
| 1 | 2.717 | 3145016 | S E | | 97.2651 | |
| 2 | 2.931 | 172 | T | | 0.0053 | |
| 3 | 3.514 | 110 | T | | 0.0034 | |
| 4 | 10.675 | 111 | | | 0.0034 | |
| 5 | 17.1 | 137 | | | 0.0042 | |
| 6 | 17.733 | 163 | | | 0.005 | |
| 7 | 17.833 | 175 | V | | 0.0054 | |
| 8 | 18.897 | 107 | V | | 0.0033 | |
| 9 | 18.981 | 146 | V | | 0.0045 | |
| 10 | 19.112 | 2821 | V | | 0.0872 | |
| 11 | 19.294 | 2108 | V | | 0.0652 | |
| 12 | 19.483 | 6988 | V | | 0.2161 | |
| 13 | 19.794 | 20792 | V | | 0.643 | |
| 14 | 19.949 | 54602 | V | | 1.6887 | |
| TOTAL | | 3233446 | | | 100 | |

| PKNO | TIME | AREA | MK | IDNO | CONC | NAME |
|---|---|---|---|---|---|---|
| 1 | 2.716 | 1898658 | S E | | 95.4276 | |
| 2 | 2.932 | 117 | T | | 0.0059 | |
| 3 | 15.6 | 213 | | | 0.0107 | |
| 4 | 17.117 | 220 | | | 0.0111 | |
| 5 | 17.762 | 263 | | | 0.0132 | |
| 6 | 17.863 | 282 | V | | 0.0142 | |
| 7 | 18.067 | 134 | V | | 0.0067 | |
| 8 | 18.839 | 110 | | | 0.0055 | |
| 9 | 18.916 | 159 | V | | 0.008 | |
| 10 | 18.997 | 214 | V | | 0.0108 | |
| 11 | 19.13 | 3668 | V | | 0.1844 | |
| 12 | 19.312 | 2724 | V | | 0.1369 | |
| 13 | 19.505 | 9033 | V | | 0.454 | |
| 14 | 19.811 | 20413 | V | | 1.026 | |
| 15 | 19.967 | 53424 | V | | 2.6851 | |
| TOTAL | | 1989631 | | | 100 | |

| PKNO | TIME | AREA | MK | IDNO | CONC | NAME |
|---|---|---|---|---|---|---|
| 1 | 2.725 | 2879081 | S E | | 96.3141 | |
| 2 | 2.934 | 151 | T | | 0.005 | |
| 3 | 10.65 | 404 | | | 0.0135 | |
| 4 | 15.444 | 357 | V | | 0.0119 | |
| 5 | 17.095 | 398 | | | 0.0133 | |
| 6 | 17.746 | 444 | | | 0.0149 | |
| 7 | 17.845 | 421 | V | | 0.0141 | |
| 8 | 18.058 | 190 | V | | 0.0064 | |
| 9 | 18.275 | 112 | V | | 0.0037 | |
| 10 | 18.414 | 120 | V | | 0.004 | |
| 11 | 18.829 | 187 | | | 0.0063 | |
| 12 | 18.903 | 230 | V | | 0.0077 | |
| 13 | 18.986 | 351 | V | | 0.0117 | |
| 14 | 19.122 | 5404 | V | | 0.1808 | |
| 15 | 19.305 | 3923 | V | | 0.1312 | |
| 16 | 19.5 | 13067 | V | | 0.4371 | |
| 17 | 19.81 | 23563 | V | | 0.7883 | |
| 18 | 19.968 | 60859 | V | | 2.0359 | |
| TOTAL | | 2989260 | | | 100 | |

ALICYCLIC DIEPOXY COMPOUND, EPOXY RESIN COMPOSITION COMPRISING THE SAME, AND CURED ARTICLE THEREFROM

TECHNICAL FIELD

The present invention relates to alicyclic diepoxy compounds. More specifically, it relates to 3,4,3',4'-diepoxybicyclohexyl compounds that contain very small amounts of isomers; epoxy resin compositions that contain the alicyclic diepoxy compounds as essential components; and cured articles obtained from the epoxy resin compositions. The epoxy resin compositions and cured articles therefrom are useful in a variety of fields including uses such as coatings, inks, coating materials, adhesives, sealants, encapsulants, resists, composite materials, transparent substrates, transparent sheets, transparent films, optical devices, optical lenses, optical members, insulating materials, stereo lithography, light emitting diode (LED) end-sealing materials, electronic papers, touch panels, solar cell substrates, optical waveguides, light-guiding panels, and holographic memories.

BACKGROUND ART

Epoxy compounds each having two alicyclic skeletons per molecule are currently available as a variety of commercial products. Typically, 3,4-epoxycyclohexylmethyl-3',4'-epoxycyclohexanecarboxylate is available from Daicel Chemical Industries, Ltd. under the trade name of "CEL-2021P"), 1,2,8,9-diepoxylimonene is available from Daicel Chemical Industries, Ltd. under trade name of "CEL-3000", and a compound corresponding to a ε-caprolactone oligomer, except with 3,4-epoxycyclohexylmethanol and 3,4-epoxycyclohexanecarboxylic acid bonded to both terminals respectively through ester bonding, is available from Daicel Chemical Industries, Ltd. under the trade name of "CEL-2081". These epoxy compounds give cured articles through reactions in the presence of various curing agents or curing catalysts. The resulting epoxy resin cured articles have properties originated from resins using compounds having alicyclic skeletons, i.e., thermal stability, transparency, and satisfactory dielectric properties. Accordingly, the epoxy resin cured articles are useful typically as components of coatings, adhesives, inks, and sealants or as intermediates for the production of other compounds that are useful for end uses including pharmaceutical preparations and articles for medical use.

However, 1,2,8,9-diepoxylimonene has methyl groups on carbon atoms constituting the epoxy groups respectively and thereby has low reactivity due to steric hindrance of the methyl groups. 3,4-epoxycyclohexylmethyl-3',4'-epoxycyclohexanecarboxylate and the compound corresponding to a ε-caprolactone oligomer, except with 3,4-epoxycyclohexylmethanol and 3,4-epoxycyclohexanecarboxylic acid bonded to both terminals respectively through ester bonding, are hydrolyzable due to their ester groups in the molecules; and cured articles obtained from these compounds may thereby suffer from deterioration in properties when used typically in hot and humid surroundings or under such conditions as to give a strong acid. Accordingly, demands are made to provide epoxy compounds containing no ester group per molecule but having alicyclic skeletons.

Such alicyclic epoxy compounds having two alicyclic skeletons per molecule but containing no ester group per molecule are disclosed typically in the following documents. For example, Japanese Unexamined Patent Application Publication (JP-A) No. 2004-99467 discloses a process for preparing a 3,4,3',4'-diepoxybicyclohexyl compound via epoxidation of a bicyclohexyl-3,3'-diene compound with an organic peroxycarboxylic acid. A Russian document (Neftekhimiya, 1972, 12, 353) discloses a process for the preparation of a 3,4,3',4'-diepoxybicyclohexyl compound via epoxidation of a bicyclohexyl-3,3'-diene compound with t-butyl hydroperoxide and a catalytic amount of molybdenum(V) chloride. JP-A No. 2004-204228 discloses a curable epoxy resin composition containing a 3,4,3',4'-diepoxybicyclohexyl compound prepared by the above preparation process, and a cured article from the epoxy resin composition. However, the epoxy resin composition containing the 3,4,3',4'-diepoxybicyclohexyl compound prepared by the preparation process shows insufficient reactivity upon curing, and the cured article therefrom has not always sufficiently satisfactory properties typically in thermal stability.

Patent Document 1: JP-A No. 2004-99467
Patent Document 2: JP-A No. 2004-204228
Non-patent Document 1: Neftekhimiya, 1972, 12, 353

DISCLOSURE OF INVENTION

Problems to be Solved by the Invention

Accordingly, an object of the present invention is to provide an alicyclic diepoxy compound or an epoxy resin composition using the same, which can give a cured article that does not suffer from deterioration in properties even when used in hot and humid surroundings or under such conditions as to give a strong acid, which show high reactivity upon curing, and which give a cured article superior in properties such as thermal stability. Another object of the present invention is to provide a cured article prepared via curing of the epoxy resin composition.

Means for Solving the Problems

After intensive investigations to achieve the above objects, the present inventors obtained the following findings. Specifically, they found that a 3,4,3',4'-diepoxybicyclohexyl compound prepared according to the known process was analyzed in detail to find that the product further contains not small amounts of isomers differing typically in positions of epoxy groups on the cyclohexane ring, in addition to the target 3,4,3',4'-diepoxybicyclohexyl compound. The fact that the product as 3,4,3',4'-diepoxybicyclohexyl compound prepared according to the known process contains large amounts of such isomers has been hitherto unknown. These isomers, if once formed, are difficult to separate from the target 3,4,3', 4'-diepoxybicyclohexyl compound, because the both are similar in physical properties such as boiling point. After investigations on the reason why the isomers are contaminated into the product, the present inventors have found that a bicyclohexyl-3,3'-diene compound used as a starting material for epoxidation contains large amounts of isomers differing in positions of double bonds. For example, when a material bicyclohexyl-3,3'-diene compound is synthetically prepared via dehydration of a 4,4'-dihydroxybicyclohexyl compound, the positional isomers are formed probably because water is by-produced and the by-produced water is repeatedly added and eliminated (detached) to cause double bonds to move to different positions. The resulting isomers, if once formed, are also difficult to separate from the bicyclohexyl-3,3'-diene compound, because the both are similar in physical properties such as boiling point. There is known a process for the preparation of a bicyclohexyl-3,3'-diene compound, in which hydrogenated biphenol (4,4'-dihydroxybicyclohexyl) is subjected to intramolecular dehydration in a solvent in the presence typically of potassium hydrogen sulfate (JP-A No. 2000-169399). This process, however, causes very large amounts of the isomers and other by-products, because the reaction is conducted while melting solid hydrogenated biphenol, by-produced water is therefore hardly eliminated from the system and resides in the system for a long time. JP-A No. 2005-97274 discloses a process for the preparation of bicyclohexyl-3,3'-diene, in which hydrogenated biphenol is subjected to intramolecular dehydration in the absence of a solvent but in the presence of an alkali metal hydrogen sulfate such as potassium hydrogen sulfate, and produced water and produced bicyclohexyl-3,3'-diene are immediately distilled off from the reactor. This process can suppress side reactions and give bicyclohexyl-3,3'-diene with a higher purity. After detail investigations of the reaction product by gas chromatography using a capillary column, however, it was found that the ratio of the target bicyclohexyl-3,3'-diene to isomers thereof is at most 80:20 even according to this process, and the reaction product contains considerable amounts of isomers. Accordingly, the present inventors further made various investigations on production processes of a bicyclohexyl-3,3'-diene compound that contains less amounts of isomers and found that intramolecular dehydration of hydrogenated biphenol under specific reaction conditions easily gives bicyclohexyl-3,3'-diene in a high yield, in which the bicyclohexyl-3,3'-diene has a very small content of isomers. They further found that epoxidation of thus obtained bicyclohexyl-3,3'-diene having such a very small content of isomers as a raw material gives 3,4,3',4'-diepoxybicyclohexyl having a very small content of isomers; and that a curable epoxy resin composition containing such 3,4,3',4'-diepoxybicyclohexyl, if cured, enables a very high curing reaction rate and, in addition, gives a cured article that has a higher glass transition temperature to thereby have significantly improved properties such as thermal stability. The present invention has been made based on these findings and further investigations.

Specifically, in the present invention, an alicyclic diepoxy compound comprises a 3,4,3',4'-diepoxybicyclohexyl compound represented by following Formula (1):

[Chemical Formula 1]

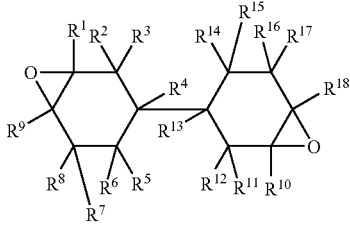

(1)

In the Formula (1), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are the same as or different from one another and each represent a hydrogen atom, a halogen atom, a hydrocarbon group which may have an oxygen atom or a halogen atom, or a substituted or unsubstituted alkoxy group. The alicyclic diepoxy compound may contain an isomer of the 3,4,3',4'-diepoxybicyclohexyl compound as an impurity. When the isomer is contained in the alicyclic diepoxy compound, a content of the isomer is less than 20% in terms of peak area ratio based on the total peak areas of the 3,4,3',4'-diepoxybicyclohexyl compound and the isomer. The peak areas are determined by gas chromatography.

Further, the present invention provides an alicyclic diepoxy compound as an epoxidation product of an alicyclic diene compound. The alicyclic diene compound comprises a bicyclohexyl-3,3'-diene compound represented by following Formula (2):

[Chemical Formula 3]

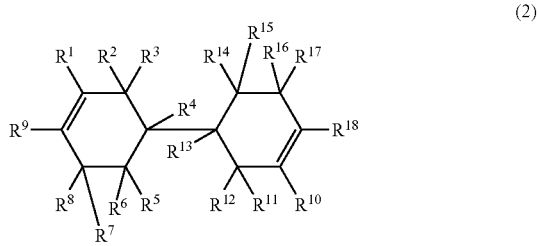

(2)

In the Formula (2), R1, R2, R3, R4, R5, R6, R7, R8, R9, R10, R11, R12, R13, R14, R15, R16, R17, and R18 are the same as or different from one another and each represent a hydrogen atom, a halogen atom, a hydrocarbon group which may have an oxygen atom or a halogen atom, or a substituted or unsubstituted alkoxy group. The bicyclohexyl-3,3'-diene compound is prepared by dehydration of a 4,4'-dihydroxybicyclohexyl compound in an organic solvent in the presence of a dehydration catalyst while distilling off by-produced water. The 4,4'-dihydroxybicyclohexyl compound is represented by following Formula (3):

[Chemical Formula 2]

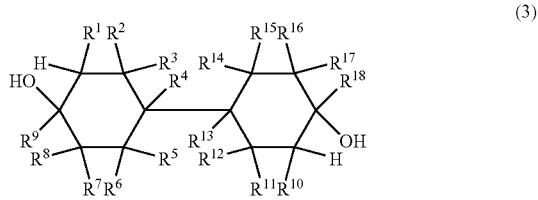

(3)

In the Formula (3), R1, R2, R3, R4, R5, R6, R7, R8, R9, R10, R11, R12, R13, R14, R15, R16, R17, and R18 are as defined above. The alicyclic diene compound may contain an isomer of the bicyclohexyl-3,3'-diene compound as an impurity, and, when the isomer is contained in the alicyclic diene compound, a content of the isomer is less than 20% in terms of peak area ratio based on the total peak areas of the bicyclohexyl-3,3'-diene compound and the isomer. The peak areas are determined by gas chromatography.

The present invention also provides an epoxy resin composition containing any of the alicyclic diepoxy compounds. The epoxy resin composition may further contain a curing agent and/or a curing catalyst.

The present invention further provides a cured article as a cured product from the epoxy resin composition.

Advantages

An epoxy resin composition containing an alicyclic diepoxy compound according to the present invention can give a cured article that does not suffer from deterioration in properties even when used in hot and humid surroundings or used under such conditions as to give a strong acid. In addition, the epoxy resin composition shows significantly improved reactivity upon curing and can be cured in a shorter time, as compared to epoxy resin compositions containing 3,4,3',4'-diepoxybicyclohexyl compounds prepared according to known processes, and gives a cured article having superior properties such as thermal stability, transparency, alkali resistance, water absorption, swelling on water absorption, and dimensional accuracy. Such a cured article according to the present invention is significantly superior in properties such as thermal stability.

BEST MODE FOR CARRYING OUT THE INVENTION

[Alicyclic Diepoxy Compounds]

Figure 1:
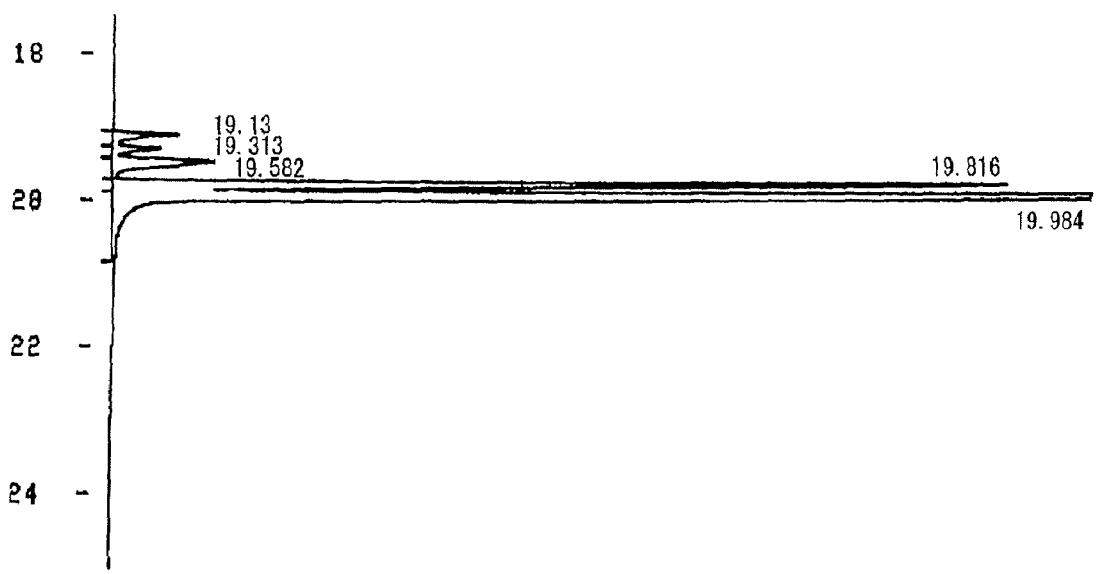
FIG. 1 depicts a gas chromatographic chart of an alicyclic diepoxy compound prepared according to Preparation Example 1.

An alicyclic diepoxy compounds according to the present invention includes a 3,4,3',4'-diepoxybicyclohexyl compound represented by the above-mentioned Formula (1) and contains isomers, as impurities, of the 3,4,3',4'-diepoxybicyclohexyl compound in a content in terms of peak area ratio of less than 20% to the total peak areas of the 3,4,3',4'-diepoxybicyclohexyl compound and the isomers thereof as determined by gas chromatography.

In Formula (1), exemplary halogen atoms as $R^1$ to $R^{18}$ include fluorine, chlorine, bromine, and iodine atom. Exemplary hydrocarbon groups in the "hydrocarbon group which may have an oxygen atom or a halogen atom" include aliphatic hydrocarbon groups, alicyclic hydrocarbon groups, aromatic hydrocarbon groups, and groups each containing two or more of these groups as bonded with each other. Exemplary aliphatic hydrocarbon groups include linear or branched-chain alkyl groups such as methyl, ethyl, propyl, isopropyl, butyl, isobutyl, t-butyl, pentyl, hexyl, octyl, and decyl groups, of which alkyl groups having about one to ten carbon atoms are preferred, and those having about one to five carbon atoms are more preferred; alkenyl groups such as vinyl and allyl groups, of which alkenyl groups having about two to ten carbon atoms are preferred, and those having about two to five carbon atoms are more preferred; and alkynyl groups such as ethynyl group, of which alkynyl groups having about two to ten carbon atoms are preferred, and those having about two to five carbon atoms are more preferred. Exemplary alicyclic hydrocarbon groups include cycloalkyl groups such as cyclopentyl and cyclohexyl groups; cycloalkenyl groups; and bridged groups. Exemplary aromatic hydrocarbon groups include phenyl and naphthyl groups. Exemplary hydrocarbon groups each having an oxygen atom include groups corresponding to the above-listed hydrocarbon groups, except with oxygen atom interposed in their carbon chain, including alkoxyalkyl groups such as methoxymethyl group and ethoxymethyl group. Exemplary hydrocarbon groups each having a halogen atom include groups corresponding to the hydrocarbon groups, except with one or more of their hydrogen atoms being replaced by halogen atoms (e.g., fluorine, chlorine, bromine, or iodine atoms), such as chloromethyl group, trifluoromethyl group, and chlorophenyl group. Exemplary alkoxy groups as the "substituted or unsubstituted alkoxy group" include alkoxy groups having about one to ten carbon atoms, such as methoxy, ethoxy, propyloxy, isopropyloxy, and butyloxy groups, of which those having about one to five carbon atoms are preferred. Exemplary substituents of the alkoxy groups include the halogen atoms.

Of 3,4,3',4'-diepoxybicyclohexyl compounds represented by Formula (1), 3,4,3',4'-diepoxybicyclohexyl in which $R^1$ to $R^{18}$ are all hydrogen atoms is particularly preferred.

It is often difficult to separate a 3,4,3',4'-diepoxybicyclohexyl compound from isomers thereof using a regular gas chromatography system, because the both are similar in physical properties such as boiling point. Accordingly, quantitative analyses of a 3,4,3',4'-diepoxybicyclohexyl compound and isomers thereof are preferably carried out by gas chromatography using a capillary column which exhibits higher separability. The quantitative analyses of a 3,4,3',4'-diepoxybicyclohexyl compound and isomers thereof by gas chromatography can be conducted under the following measuring conditions. The structures of the 3,4,3',4'-diepoxybicyclohexyl compound and the isomers thereof may be identified typically by NMR, GC-MS, and/or gas chromatography-infrared spectrometry (GC-IR).

Measuring instrument: HP 6890 (supplied by Hewlett-Packard Company)
Column: HP-5, 30 m in length, 0.25 μm in membrane thickness, 0.32 mm in inner diameter
Liquid phase: 5%-Diphenyl-95%-dimethylpolysiloxane
Carrier gas: Nitrogen
Carrier gas flow rate: 1.0 ml/minute
Detector: Flame ionization detector (FID)
Inlet temperature: 250° C.
Detector temperature: 300° C.
Temperature rise pattern (column): Holding at 100° C. for 2 minutes, heating at 5° C./minute to 300° C., and holding at 300° C. for 10 minutes
Split ratio: 100
Sample: 1 μl (epoxy compound:acetone=1:40)

In an alicyclic diepoxy compound according to the present invention, the content of isomers, as impurities, of the 3,4,3',4'-diepoxybicyclohexyl compound is less than 20%, for example, 18.5% or less, preferably 18% or less, and more preferably 16% or less, based on the total of the 3,4,3',4'-diepoxybicyclohexyl compound (main compound) and the isomers thereof, in terms of peak area ratio as determined by gas chromatography. The alicyclic diepoxy compound is remarkably fast curable and gives a cured article that has a significantly higher glass transition temperature and shows dramatically improved properties such as thermal stability, as compared to a compound having a content of the isomers of 20% or more.

The alicyclic diepoxy compound according to the present invention can be prepared typically by subjecting an alicyclic diene compound to epoxidation, where the alicyclic diene compound includes a bicyclohexyl-3,3'-diene compound represented by the above-mentioned Formula (2), in which the content of isomers (isomers differing in positions of double bonds) of the bicyclohexyl-3,3'-diene compound is less than 20%, for example, 18.5% or less, preferably 18% or less, more preferably 16% or less, and particularly preferably 15% or less, based on the total of the bicyclohexyl-3,3'-diene compound and the isomers thereof, in terms of peak area ratio as determined by gas chromatography. In Formula (2), $R^1$ to $R^{18}$ are as defined above.

The bicyclohexyl-3,3'-diene compound, represented by Formula (2), having a less isomer content and used herein as a raw material can be prepared, for example, by subjecting a 4,4'-dihydroxybicyclohexyl compound represented by the above-mentioned Formula (3) to dehydration in an organic solvent in the presence of a dehydration catalyst while distilling off by-produced water. In Formula (3), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ are as defined above.

More specifically, the compound can be prepared typically by a process which includes the step (i) of heating a 4,4'-dihydroxybicyclohexyl compound represented by the above-mentioned Formula (3) at a temperature of from 130° C. to 230° C. and a pressure greater than 20 Torr (2.67 kPa) in an organic solvent in the presence of a dehydration catalyst to carry out dehydration of the 4,4'-dihydroxybicyclohexyl compound while distilling off by-produced water, in which the dehydration catalyst is liquid or soluble in a reaction liquid under the reaction conditions; and the subsequent step (ii) of heating the resulting reaction mixture liquid at a temperature of from 50° C. to 220° C. and a pressure of 200 Torr (26.7 kPa) or less to thereby recover a product bicyclohexyl-3,3'-diene compound represented by Formula (2) as a distillate. This process will be illustrated below.

A representative example of compounds represented by Formula (3) includes 4,4'-dihydroxybicyclohexyl (hydrogenated biphenol).

Organic solvents for use in the step (i) are not particularly limited, as long as being solvents that are inert (inactive) under the reaction conditions, but are preferably those that are liquid at 25° C. and have a boiling point of about 120° C. to about 200° C. Representative examples of preferred organic solvents include aromatic hydrocarbons such as xylenes, cumene, and pseudocumene; and aliphatic hydrocarbons such as dodecane and undecane. For separating and removing by-product water in a simple manner, organic solvents that are azeotropic with water and are separable from water may be used as the organic solvent. Ketones, esters, and other solvents that undergo a reaction in the presence of an acid are undesirable herein, even when they have a boiling point within the above-specified range. Alcohol solvents are also undesirable, because they may undergo dehydration.

The amount of organic solvents can be suitably set in consideration typically of operational ease (operability) and reaction rate, but is generally about 50 to 1000 parts by weight, preferably about 80 to 800 parts by weight, and more preferably about 100 to 500 parts by weight, to 100 parts by weight of the substrate of 4,4'-dihydroxybicyclohexyl compound.

Dehydration catalysts for use in the step (i) are not particularly limited, as long as having a dehydration activity and being liquid or soluble in a reaction liquid (fully soluble in the reaction liquid in the amount as described later), but are preferably those having no or a least possible activity on the reaction solvents. The dehydration catalysts that are liquid under the reaction conditions, are preferably those that are finely dispersed in the reaction liquid. Exemplary generally-used dehydration catalysts include acids including inorganic acids such as phosphoric acid and sulfuric acid, sulfonic acids such as p-toluenesulfonic acid, benzenesulfonic acid and naphthalenesulfonic acid, and the like; and salts of them, typified by fully neutralized salts and partially neutralized salts of the acids with organic bases. Each of different dehydration catalysts may be used alone or in combination.

When a neutralized salt of an acid with an organic base is used, the neutralized salt (fully neutralized salt or partially neutralized salt) may be isolated and purified from a reaction mixture obtained as a result of a reaction between the acid and the organic base, but the reaction mixture obtained as a result of a reaction between the acid and the organic base and containing a fully neutralized salt and/or a partially neutralized salt may also be used as intact as the neutralized salt. In the latter case, it is acceptable that the reaction mixture further contains a free acid. In the latter case, the ratio between the acid and the organic base may be such that the amount of the organic base is, for example, about 0.01 to 1 equivalent, preferably about 0.05 to 0.5 equivalent, and more preferably about 0.1 to 0.47 equivalent, to 1 equivalent of the acid. Typically, when a reaction mixture between sulfuric acid and an organic base is used, the ratio between sulfuric acid and the organic base may be such that the amount of the organic base is preferably about 0.02 to 2 moles, more preferably about 0.1 to 1.0 mole, and particularly preferably about 0.2 to 0.95 mole, to 1 mole of sulfuric acid. A neutralized salt of an acid with an organic base, if used, may be formed within the system by independently adding the acid and the organic base to the system.

The organic base can be any organic compound having basicity, and exemplary organic bases include amines such as 1,8-diazabicyclo[5.4.0]undecene-7 (DBU), 1,5-diazabicyclo[4.3.0]nonene-5 (DBN), 1,4-diazabicyclo[2.2.2]octane, piperidine, N-methylpiperidine, pyrrolidine, N-methylpyrrolidine, triethylamine, tributylamine, trioctylamine, benzyldimethylamine, 4-dimethylaminopyridine, and N,N-dimethylaniline, of which tertiary amines are preferred; nitrogen-containing aromatic heterocyclic compounds such as pyridine, collidine, quinoline, and imidazole; guanidines; and hydrazines. Among them, preferred are tertiary amines such as 1,8-diazabicyclo[5.4.0]undecene-7 (DBU), 1,5-diazabicyclo[4.3.0]nonene-5 (DBN), triethylenediamine, and triethylamine (of which cyclic amines are more preferred); guanidines; and hydrazines; of which DBU, DBN, triethylenediamine, and triethylamine are more preferred. Of such organic bases, preferred are those having a pKa of 11 or greater and those having a boiling point of 150° C. or higher.

Use of an alkali metal salt of sulfuric acid, such as potassium hydrogen sulfate, as the dehydration catalyst fails to give a bicyclohexyl-3,3'-diene compound in which the content of isomers of the bicyclohexyl-3,3'-diene compound is less than 20% based on the total of the bicyclohexyl-3,3'-diene compound and the isomers thereof in terms of peak area ratio as determined by gas chromatography. In this connection, use of ammonium hydrogen sulfate as the dehydration catalyst gives a bicyclohexyl-3,3'-diene compound in which the content of isomers of the bicyclohexyl-3,3'-diene compound of about 19% based on the total of the bicyclohexyl-3,3'-diene compound and the isomers thereof in terms of peak area ratio as determined by gas chromatography.

Accordingly, preferred dehydration catalysts include sulfonic acids (e.g., p-toluenesulfonic acid), phosphoric acid, sulfuric acid, fully neutralized salts or partially neutralized salts of sulfonic acids (e.g., p-toluenesulfonic acid) with organic bases, fully neutralized salts or partially neutralized salts of phosphoric acid with organic bases, and fully neutralized salts or partially neutralized salts of sulfuric acid with organic bases. Among them, more preferred are sulfonic acids (of which p-toluenesulfonic acid is typically preferred), fully neutralized salts or partially neutralized salts of the sulfonic acids with organic bases, fully neutralized salts or partially neutralized salts of sulfuric acid with organic bases, and mixtures of these with sulfuric acid; of which further preferred are fully neutralized salts or partially neutralized salts (of which partially neutralized salts are more preferred) of sulfuric acid with organic bases, and mixtures of these with sulfuric acid.

The amount of dehydration catalysts is, for example, 0.001 to 0.5 mole, preferably 0.001 to 0.47 mole (e.g., 0.001 to 0.3 mole), and more preferably 0.005 to 0.45 mole (e.g., 0.005 to 0.2 mole), to 1 mole of the material 4,4'-dihydroxybicyclohexyl compound represented by Formula (3).

Procedures, such as order and way, for adding the material 4,4'-dihydroxybicyclohexyl compound represented by Formula (3), the organic solvent, and the dehydration catalyst in the step (i) (dehydration step) are not particularly limited. A reaction may be started after charging the whole quantities of the components such as the 4,4'-dihydroxybicyclohexyl compound represented by Formula (3) and the dehydration catalyst into the reaction system, or the reaction may be carried out while adding these components intermittently or continuously to the reaction system. More specifically but by way of example, a possible process includes preparing a mixture of a 4,4'-dihydroxybicyclohexyl compound represented by Formula (3), a dehydration catalyst that is liquid or soluble in a reaction liquid under the reaction conditions, and an organic solvent; and heating the mixture at a temperature of from 130° C. to 230° C. and a pressure greater than 20 Torr (2.67 kPa) to carry out dehydration while distilling off by-produced water. In another possible process, dehydration is carried out by intermittently or continuously adding a 4,4'-dihydroxybicyclohexyl compound represented by Formula (3) to an organic solvent at a pressure greater than 20 Torr (2.67 kPa) while distilling off by-product water, in which the organic solvent is heated at a temperature of from 130° C. to 230° C. and is coexistent with the dehydration catalyst that is liquid or soluble in a liquid reaction mixture under the reaction conditions. The latter process is a process of carrying out dehydration by intermittently or continuously adding the alicyclic alcohol to the organic solvent in the presence of the dehydration catalyst while distilling off by-product water (hereinafter briefly referred to as "alicyclic alcohol sequential addition process"). The latter process gives a great advantage of noticeably suppressing by-production of high-boiling impurities to yield the target compound in a significantly improved yield. This is probably because the 4,4'-dihydroxybicyclohexyl compound represented by Formula (3) does not accumulate in the reaction system according to this process, whereby side reactions can be suppressed. Exemplary side reactions include etherification; dimerization and polymerization (multimerization) via addition of hydroxyl groups typically of the material 4,4'-dihydroxybicyclohexyl compound represented by Formula (3) to double bonds of dehydration products such as a target cyclic olefin compound and a reaction intermediate having both a double bond and a hydroxyl group; and polymerization at the double bonds. In the alicyclic alcohol sequential addition process, the time period until the whole quantity of the 4,4'-dihydroxybicyclohexyl compound represented by Formula (3) is added to the reaction system may be suitably set in consideration typically of the operational ease and reaction rate, but is generally from 10 minutes to 25 hours, preferably from 15 minutes to 12 hours, and more preferably from 20 minutes to 6 hours.

The step (i) and the step (ii) differ from each other in the pressure. The reaction liquid in the step (i) contains an unreacted 4,4'-dihydroxybicyclohexyl compound, a reaction intermediate in which only one of the two hydroxylated-cyclohexane rings of the 4,4'-dihydroxybicyclohexyl compound has undergone intramolecular dehydration into a cyclohexene ring, the target bicyclohexyl-3,3'-diene compound, by-produced water, the dehydration catalyst, and the reaction solvent in coexistence. In the step (i), the by-product water is distilled out (evaporated), but it is not desirable to distill out the reaction intermediate in this step for the following reasons. Specifically, (1) distilling out of the reaction intermediate causes reduction in the yield of the target compound, because the reaction intermediate can be converted into the target compound via further intramolecular dehydration; and (2) the reaction intermediate is generally a sublimable solid, and such a sublimated reaction intermediate may deposit in a pathway for distillation of by-product water in a distillation column, if used, to block or clog the distillation pathway, and this may cause increase in the inner pressure of the reactor, thus causing troubles such as a rupture or damage of the reactor and scattering of the reaction liquid. Accordingly, dehydration in the step (i) is carried out, while distilling off by-product water, at a pressure greater than 20 Torr (2.67 kPa) so as to avoid distillation of the reaction intermediate. The pressure is preferably greater than 20 Torr and equal to or less than normal pressure (atmospheric pressure) (greater than 2.67 kPa and equal to or less than 0.1 MPa), more preferably greater than 100 Torr and equal to or less than normal pressure (greater than 13.3 kPa and equal to or less than 0.1 MPa), and further preferably greater than 200 Torr and equal to or less than normal pressure (greater than 26.7 kPa and equal to or less than 0.1 MPa). From the viewpoint of operational ease, the pressure is typically preferably normal pressure (atmospheric pressure). The temperature (reaction temperature) in the step (i) is from 130° C. to 230° C. (e.g., 130° C. to 200° C.), preferably from 140° C. to 200° C. (e.g., 140° C. to 195° C.), and more preferably from 140° C. to 185° C. Dehydration at an excessively high temperature may cause side reactions such as isomerization, and dehydration at an excessively low temperature may cause an insufficient reaction rate. The reaction period is, for example in the case of preparation on the order of about 3 liters, from about 1 to 10 hours, and preferably from about 2 to 6 hours. In the alicyclic alcohol sequential addition process, the reaction period from the time point upon the completion of the addition of the starting material is, for example, from about 0.5 to 10 hours, and preferably from about 1 to 6 hours.

In the step (ii), the target bicyclohexyl-3,3'-diene compound is recovered as a distillate from a reaction mixture from which by-produced water has been distilled out. The reaction mixture obtained in the step (i) may be subjected to the step (ii) without any treatment, but, if necessary, the reaction mixture may be subjected to a suitable treatment such as extraction, washing with water, and/or adjustment in acidity or alkalinity before subjected to the step (ii). Generally, when an organic solvent used in the reaction has a boiling point lower than that of the target bicyclohexyl-3,3'-diene compound, the bicyclohexyl-3,3'-diene compound is recovered as a distillate after distilling off the organic solvent.

The step (ii) can be carried out at a pressure of 200 Torr (26.7 kPa) or less, because there is only a small amount of the reaction intermediate in the step (ii), and even a low pressure may not cause problems such as blockage of the distillation pathway; and a high pressure may require a longer time period to recover the target compound as a distillate. The pressure in the step (ii) is preferably set lower than the pressure in the step (i). Typically, the different between the pressure in the step (i) and the pressure in the step (ii) [the former minus the latter] may be, for example, 100 Torr or more (13.3 kPa or more), preferably 200 Torr or more (26.7 kPa or more), and more preferably 500 Torr or more (66.7 kPa or more). The pressure in the step (ii) is preferably from about 3 to 200 Torr (from about 0.40 to 26.7 kPa), more preferably from about 3 to 100 Torr (from about 0.40 to 13.3 kPa), and further preferably from about 3 to 20 Torr (from about 0.40 to 2.67 kPa). The temperature in the step (ii) is from 50° C. to 220° C. (e.g., 100° C. to 220° C.), and preferably from 140° C. to 220° C. (e.g., 150° C. to 200° C.). The temperature in the step (ii) may also be selected within a range of from 120° C. to 180° C., and preferably within a range of from 130° C. and lower than 150° C. An excessively high process temperature may often cause occurrence of side reactions and deterioration in yield of the bicyclohexyl-3,3'-diene compound. In contrast, an excessively low process temperature may cause an insufficient distillation rate.

A distillation apparatus, if attached typically to a reactor for the distillation typically of the target bicyclohexyl-3,3'-diene compound, is not particularly limited, as long as being a distillation apparatus that is commonly or generally used, such as a packed column or an Oldershaw distillation column, and having a satisfactory reflux ratio.

The bicyclohexyl-3,3'-diene compound recovered as a distillate in the step (ii) can further be purified according to necessity. When the distilled bicyclohexyl-3,3'-diene compound contains a trace amount of water, the target bicyclohexyl-3,3'-diene compound can be purified and separated by using the difference in specific gravity. In general, however, purification by distillation is preferred.

According to this process, a starting material 4,4'-dihydroxybicyclohexyl compound is reacted, while distilling off by-product water, under specific reaction conditions in an organic solvent in the presence of a dehydration catalyst that is liquid or soluble in a reaction liquid under the reaction conditions; and the resulting bicyclohexyl-3,3'-diene compound is distilled under specific conditions to recover as a distillate. The target reaction can thereby be conducted at a relatively low temperature within a relatively short period, side reactions such as isomerization can be suppressed, and problems or disadvantages, such as loss due to distillation out of a reaction intermediate and blockage due to sublimation of the reaction intermediate, are prevented. Accordingly, a high-purity bicyclohexyl-3,3'-diene compound containing, if any, less impurities can be efficiently and simply obtained in a high yield. Specifically, there can be obtained an alicyclic diene compound in which the content of isomers of a bicyclohexyl-3,3'-diene compound represented by Formula (2) is less than 20% (e.g., 18.5% or less, preferably 18% or less, more preferably 16% or less, and particularly preferably 15% or less) based on the total of the bicyclohexyl-3,3'-diene compound and the isomers thereof in terms of peak area ratio as determined by gas chromatography.

In contrast, known processes typified by the process described in JP-A No. 2000-169399 require a long reaction period, and this invites large amounts of undesirable by-products as a result of side reactions such as isomerization. Such by-product isomers have physical properties, such as boiling point and solubility in an solvent, similar to those of the target compound, and once they are formed, it is very difficult to separate them from the target compound. If a product cyclic olefin compound containing large amounts of such by-products is used as a curable resin typically after epoxidation, the by-products contained therein may cause an insufficient reactivity of the resin upon curing and may fail to provide a cured article superior in properties such as thermal stability. In this connection, the isomers are difficult to be separated from the bicyclohexyl-3,3'-diene compound with a regular gas chromatographic system, because the both are very similar in physical properties such as boiling point, and the yield and purity of the bicyclohexyl-3,3'-diene compound have been indicated higher than their actual values in past documents. Accordingly, the bicyclohexyl-3,3'-diene compound and the isomers thereof are preferably analyzed by gas chromatography using a capillary column which exhibits higher separability.

Quantitative analyses of a bicyclohexyl-3,3'-diene compound and isomers thereof by using gas chromatography can be carried out under the following measuring conditions. The structures of the bicyclohexyl-3,3'-diene compound and the isomers thereof can be identified typically by NMR, gas chromatography-mass spectrometry (GC-MS), and/or gas chromatography-infrared spectrometry (GC-IR).

Measuring instrument: HP 6890 (supplied by Hewlett-Packard Company)
Column: HP-5, 60 m in length, 0.32 mm in inner diameter
Liquid phase: 5%-diphenyl-95%-dimethylpolysiloxane
Carrier gas: Nitrogen
Carrier gas flow rate: 2.6 ml/minute
Detector: FID
Inlet temperature: 250° C.
Detector temperature: 250° C.
Temperature rise pattern (column): Holding at 60° C. for 5 minutes, and heating to 300° C. at a rate of 10° C./minute
Split ratio: 100
Sample: 1 µl The way to epoxidize the bicyclohexyl-3,3'-diene compound is not particularly limited and can be any of, for example, a process of using an organic peroxycarboxylic acid as an oxidizing agent (epoxidizing agent); and a process of using a hydroperoxide, such as t-butyl hydroperoxide, and a metallic compound, such as a molybdenum compound. Among such processes, the process of using an organic peroxycarboxylic acid is preferred from the viewpoints of safety, cost efficiency, and yield. This process will be illustrated below.

Exemplary usable organic peroxycarboxylic acids include performic acid, peroxyacetic acid, peroxybenzoic acid, peroxyisobutyric acid, and peroxytrifluoroacetic acid. Of organic peroxycarboxylic acids, peroxyacetic acid is particularly preferred as an epoxidizing agent, for its high reactivity and high stability. Of such organic peroxycarboxylic acids, those containing substantially no water, specifically, those having a water content of 0.8 percent by weight or less, and preferably 0.6 percent by weight or less, are preferred. These are preferred so as to give compounds having a high degree of epoxidation. Organic peroxycarboxylic acids containing substantially no water are prepared via oxidation of aldehydes, such as acetaldehyde, with air. Typically, peroxyacetic acid may be prepared by the process described in German Unexamined Patent Application Publication (DE-A) No. 1418465 and JP-A No. Sho 54-3006. According to this process, an organic peroxycarboxylic acid can be substantially inexpensively obtained, because it can be continuously synthetically prepared in a larger amount in a higher concentration than the preparation of an organic peroxycarboxylic acid by synthesizing the aliphatic peroxycarboxylic acid from hydrogen peroxide and extracting the aliphatic peroxycarboxylic acid with a solvent.

The amount of an epoxidizing agent is not strictly limited, and an optimum amount in each case is determined depending typically on parameters such as reactivity between an individual epoxidizing agent and a bicyclohexyl-3,3'-diene compound. The amount of an epoxidizing agent is, for example, about 1.0 to 3.0 moles, and preferably about 1.05 to 1.5 moles, to 1 mole of unsaturated groups. Use of an epoxidizing agent in an amount greater than 3 times by mole is generally disadvantageous in view of economical efficiency and occurrence of side reactions.

Epoxidation is carried out while determining whether or not a solvent is used and adjusting the reaction temperature depending on the apparatus to be used and the properties of starting material. The solvent can be used in order to reduce the viscosity of the starting material and stabilize the epoxidizing agent as a result of dilution. When peroxyacetic acid is used as an epoxidizing agent, usable solvents include esters, aromatic compounds, and ethers. Among them, preferred solvents include ethyl acetate, hexane, cyclohexane, toluene, and benzene, of which ethyl acetate is more preferred. The reaction temperature is determined depending on the reactivity between the employed combination of an epoxidizing agent and a bicyclohexyl-3,3'-diene compound. By way of example, when peroxyacetic acid is used, a reaction is preferably carried out at a temperature of from 20° C. to 70° C. A reaction, if carried out at a temperature lower than 20° C., may proceed too slowly; and a reaction, if carried out at a temperature higher than 70° C., may cause decomposition of peroxyacetic acid with heat generation, thus being undesirable.

There is no need of subjecting a crude reaction mixture to a special operation. Typically, the crude reaction mixture may be aged by stirring for one to five hours. Isolation of a target epoxy compound from the resulting crude reaction mixture can be carried out according to a suitable isolation procedure. Exemplary procedures herein include precipitation from a poor solvent; addition of the epoxy compound to stirred hot water and removal of the solvent by distillation; direct desolvation; and purification by distillation.

Thus, there can be obtained an alicyclic diepoxy compound in which the content of isomers (isomer percentage) of a 3,4,3',4'-diepoxybicyclohexyl compound represented by Formula (1) is less than 20% (e.g., 18.5% or less, preferably 18% or less, and more preferably 16% or less), based on the total of the 3,4,3',4'-diepoxybicyclohexyl compound represented by Formula (1) and the isomers thereof in terms of peak area ratio as determined by gas chromatography.

Alicyclic diepoxy compounds according to the present invention can thereby give various coatings, inks, adhesives, sealants, molded articles, and constitutive materials thereof, and intermediates for them, by subjecting the compounds to homopolymerization, copolymerization, reactions with other compounds, or reactions in the presence of other oligomers or polymers. Exemplary end uses using the alicyclic diepoxy compounds include acid removers, furniture coatings, ornament coatings, undercoatings and finish coatings for automobiles, coatings for beverage cans and other cans, ultraviolet-curable inks for alphabetic information or image information, protecting films of optical disc recording layers, protecting films for color filters in display members, adhesives for bonding of optical discs, adhesives for bonding between optical materials, die bonding of semiconductor devices, sealing materials for organic electroluminescence (organic EL) displays, end-sealing materials for light emitting diodes (LED), touch panels, electronic papers, microlenses, microelectromechanical systems (MEMS), optical waveguides, light-guiding panels, photoresists suitable for the development of printing matrices or printed circuit boards, casting printing rolls, molded articles made from molding compositions or sheet-forming compositions that mainly contain an unsaturated polyester and styrene and are reinforced by a fiber made of glass, carbon, graphite, or another material, solvents, flame retardants, pharmaceutical preparations, and articles for medical use. The compounds can also be used as intermediates for the preparation of other compounds that are useful for these and other end uses. The cured resins made from the alicyclic diepoxy compounds of the present invention can have thermal stability, transparency, and satisfactory dielectric properties, where these properties are features of resins using compounds having alicyclic skeletons.

[Epoxy Resin Compositions]

Epoxy resin compositions according to the present invention each contain an alicyclic diepoxy compound according to the present invention as a main ingredient (epoxy compound). Typically, these epoxy resin compositions can be cured more quickly (at a higher curing rate) and can give, as a result of curing, cured articles having higher glass transition temperatures and having significantly superior properties such as thermal stability, as compared with known equivalents.

The epoxy resin compositions can be used as curable epoxy resin compositions by further containing a curing agent and/or a curing catalyst.

Curing agents for use herein are not specifically limited and can be freely selected from among those commonly used as curing agents for epoxy resins. Among such curing agents, acid anhydrides are preferred. Of acid anhydrides, preferred are those that are liquid at ordinary temperature, such as methyltetrahydrophthalic anhydride, methylhexahydrophthalic anhydride, dodecenylsuccinic anhydride, and endomethylenemethyltetrahydrophthalic anhydride. Acid anhydrides that are solid at ordinary temperature can be used within ranges not adversely affecting the impregnation properties of the epoxy resin compositions. Exemplary acid anhydrides that are solid at ordinary temperature include phthalic anhydride, tetrahydrophthalic anhydride, hexahydrophthalic anhydride, and methylcyclohexenedicarboxylic anhydride. Such an acid anhydride that is solid at ordinary temperature is, if used, preferably dissolved in another acid anhydride that is liquid at ordinary temperature, to give a mixture that is liquid at ordinary temperature and used in the form of this mixture. Of acid anhydrides, preferred are acid anhydrides each having one or two aliphatic or aromatic rings per molecule, having one or two acid anhydride groups, and containing about four to twenty-five, and preferably about eight to twenty carbon atoms.

The amount of curing agents is, for example, 50 to 300 parts by weight, and preferably 100 to 200 parts by weight, to 100 parts by weight of epoxy compounds (typified by alicyclic diepoxy compounds according to the present invention) in the epoxy resin composition. More specifically, the amount of curing agents is preferably an effective amount to exhibit actions as a curing agent, namely, the amount is preferably such that the amount of acid anhydrides is 0.3 to 1.5 equivalents to 1 equivalent of epoxy groups in epoxy compounds. Curing agents, if used in an excessively small amount, may cause insufficient curing of the composition. In contrast, curing agents, if used in an excessively large amount, may cause deterioration in properties of the resulting cured article.

Accelerators may be used in combination with the curing agents. As used herein "accelerators" refer to compounds that act to promote or accelerate a curing reaction when an epoxy compound is cured by the action of an acid anhydride. Such accelerators are not particularly limited, as long as being generally-used accelerators, and exemplary accelerators include diazabicycloundecene accelerators; phosphorus accelerators such as phosphoric acid esters and phosphines; and amine accelerators such as tertiary amines and quaternary ammonium salts.

Exemplary diazabicycloundecene accelerators include 1,8-diazabicyclo[5.4.0]undecene-7 (DBU) and salts thereof, of which octanoic acid salt and sulfonic acid salt of 1,8-diazabicyclo[5.4.0]undecene-7 are particularly preferred. Specific examples of the other accelerators include any known compounds including tertiary amine such as benzyldimethylamine and 2,4,6-tris(dimethylaminomethyl)phenol; imidazoles such as 2-ethyl-4-methylimidazole and 1-cyanoethyl-2-ethyl-4-methylimidazole; organic phosphine compounds such as triphenylphosphine; tertiary amine salts; quaternary ammonium salts; phosphonium salts; and metal salts such as tin octoate.

The amount of accelerators may be 0.05 to 5 parts by weight, and preferably 0.1 to 3 parts by weight, to 100 parts by weight of epoxy compounds (typified by alicyclic diepoxy compounds according to the present invention) in the epoxy resin composition. Accelerators, if contained in an amount of less than 0.05 part by weight, may not sufficiently accelerate curing. In contrast, accelerators, if contained in an amount of greater than 5 parts by weight, may adversely affect properties, such as hue or color, of the cured article.

If necessary, a hydroxyl-containing compound may be added so as to proceed the reaction gradually. Exemplary hydroxyl-containing compounds include ethylene glycol, diethylene glycol, glycerol, and trimethylolpropane.

Exemplary curing catalysts include cationic polymerization initiators; and free-radical polymerization initiators (in the cases where free-radical polymerizable compounds are contained). Cationic polymerization initiators include heat-induced cationic polymerization initiators and photo-induced cationic polymerization initiators. As used herein "photo-induced cationic polymerization initiators" refer to initiators that release a substance to initiate cationic polymerization upon application of light, and "heat-induced cationic polymerization initiators" refer to initiators that release a substance to initiate cationic polymerization as a result of heating. Exemplary usable photo-induced cationic polymerization initiators include compounds such as sulfonium salts, iodonium salts, diazonium salts, and allene-ion complexes. Specific examples thereof include sulfonium salt compounds such as "UVACURE 1590" (supplied by Daicel-Cytec Co., Ltd.), "DAICAT 11" (supplied by Daicel Chemical Industries, Ltd.), "CD-1011" (supplied by Sartomert Co., Inc.), and "SI-60L", "SI-80L", and "SI-100L" (each supplied by Sanshin Chemical Industry Co., Ltd.); iodonium salt compounds such as "DAICAT 12" (supplied by Daicel Chemical Industries, Ltd.) and "CD-1012" (supplied by Sartomert Co., Inc.); and diazonium salt compounds such as "SP-150" and "SP-170" (each supplied by ADEKA CORPORATION).

Exemplary heat-induced cationic polymerization initiators include aryldiazonium salts such as "PP-33" supplied by ADEKA CORPORATION); aryliodonium salts; arylsulfonium salts such as "FC-509" supplied by Minnesota Mining & Manufacturing Co. (3M), "UVE 1014" supplied by General Electric Co., Ltd., "CP-66" and "CP-77" supplied by ADEKA CORPORATION, and "SI-60L", "SI-80L", "SI-100L", and "SI-110L" supplied by Sanshin Chemical Industry Co., Ltd.; and allene-ion complexes such as "CG-24-61" supplied by Ciba Geigy Ltd. Exemplary heat-induced cationic polymerization initiators further include systems containing a silanol or phenol compound and a chelate compound of a metal, such as aluminum or titanium, with an acetoacetic ester or diketone. Exemplary chelate compounds include aluminum trisacetylacetonate and aluminum tris(ethyl acetoacetate). Exemplary silanol or phenol compounds include triphenylsilanol and bisphenol-S.

The amount of curing catalysts is, for example, from 0.01 to 20 parts by weight, preferably from 0.05 to 10 parts by weight, and more preferably from 0.1 to 5 parts by weight, to 100 parts by weight of epoxy compounds (typified by alicyclic diepoxy compounds according to the present invention) in the epoxy resin composition. Use of curing catalysts within this range gives cured articles that are further superior typically in thermal stability, transparency, and weather resistance. Curing catalysts, if used in an excessively small amount, may not sufficiently help the composition to be cured. In contrast, curing catalysts, if used in an excessively large amount, may cause deterioration of properties of a cured article.

Epoxy resin compositions according to the present invention may further contain additives within ranges not adversely affecting properties such as viscosity and optical transparency. The additives can be a variety of additives which have been commonly used for epoxy resin compositions. Exemplary additives include silicone- or fluorine-containing defoaming agents; silane coupling agents such as γ-glycidoxypropyltrimethoxysilane; fillers; flame retardants; antioxidants; ultraviolet-absorbers; ion-adsorbents; colorants; pigments; stress-reducing agents; flexibility-imparting agents; waxes; halogen-trapping agents; leveling agents; and wettability improvers.

Epoxy resin compositions according to the present invention may further contain one or more epoxy compounds other than alicyclic diepoxy compounds according to the present invention [compounds other than the compounds represented by Formula (1) and isomers thereof]. In this case, the amount of alicyclic diepoxy compounds according to the present invention is, for example, 30 percent by weight or more, preferably 40 percent by weight or more, more preferably 50 percent by weight or more, and particularly preferably 60 percent by weight or more, based on the total amount of epoxy compounds. In addition or alternatively, the epoxy resin compositions may further contain one or more free-radical polymerizable compounds. Where necessary, the epoxy resin compositions may further contain other components such as thermoplastic resins, synthetic rubbers, elastomers, thermosetting resins, and organic or inorganic nanoparticles.

Epoxy resin compositions according to the present invention may be prepared by mixing and stirring the alicyclic diepoxy compounds of the present invention and, where necessary, the respective components mentioned above, using a mixer such as a blender. The mixing/stirring temperature is generally preferably set at about 10° C. to 60° C., while it may vary depending typically on the types of curing agents and curing catalysts to be used. If the preparation is carried out at a set temperature lower than 10° C., the components may show an excessively high viscosity, and this may impede homogeneous stirring and mixing of the components; and in contrast, if the preparation is carried out at an excessively high set temperature, a curing reaction may occur to fail to provide a normal epoxy resin composition, thus being undesirable. The stirring and mixing may be carried out using a commonly-used apparatus such as a single-screw or multiple-screw extruder equipped with a pressure reducing device; a kneader; or a dissolver, typically for a duration of about 10 minutes to prepare an epoxy resin composition.

[Cured Articles]

Cured articles according to the present invention are obtained by curing the epoxy resin compositions according to the present invention. The means of curing may be any means such as heat or light. When thermal curing (heat-induced curing) is conduced using a heat-induced cationic polymerization initiator, the curing temperature is, for example, 30° C. to 240° C., and preferably 35° C. to 200° C. Curing may be conducted through two steps. Typically, thermal curing (heat-induced curing), if conducted using a heat-induced cationic polymerization initiator, may be conducted by carrying out primary curing at a temperature of from 30° C. to 100° C., and preferably from 30° C. to 80° C.; and thereafter carrying out secondary curing at a temperature of from 110° C. to 240° C., preferably from 120° C. to 200° C., so as to yield a cured article that is satisfactory in properties such as transparency and thermal stability.

When curing is conducted using a curing agent such as an acid anhydride, the curing temperature is, for example, from 30° C. to 240° C., and preferably from 50° C. to 200° C. Also in this case, curing may be conducted through two steps. Typically, curing may be conducted by carrying out primary curing at a temperature of from 30° C. to 130° C., and preferably 50° C. to 130° C.; and thereafter carrying out secondary curing at a temperature of from 135° C. to 240° C., preferably from 135° C. to 200° C., so as to yield a cured article that is satisfactory in properties such as transparency and thermal stability.

When curing is conducted via photo-induced curing using a photo-induced cationic polymerization initiator, the light to be used may be active energy rays such as ultraviolet rays and electron beams. Typically, when curing is conducted by the application of an ultraviolet ray, exemplary light sources include high-pressure mercury lamps, ultrahigh-pressure mercury lamps, carbon arc lamps, xenon lamps, metal halide lamps, and light-emitting diodes (LED). The irradiation time is at longest several tens of seconds, and generally several seconds, while it may vary depending on conditions such as the type of light source and the distance between the light source and a plane to be applied. If necessary, heating may be carried out after the application of ultraviolet ray, so as to complete the curing. An irradiation source with an output of lamp of about 80 to 300 W/cm is generally used. Electron beam application, if employed, is preferably carried out using an electron beam with energy of from 50 to 1000 KeV at an irradiation level of 2 to 5 Mrad.

In the present invention, epoxy resin compositions and cured articles therefrom have satisfactory transparency and high glass transition temperatures and are thereby useful in a variety of fields including uses such as coatings, inks, coating materials, adhesives, sealants, encapsulants, resists, composite materials, transparent substrates, transparent sheets, transparent films, optical devices, optical lenses, optical members, insulating materials, stereo lithography, LED end-sealing materials, electronic papers, touch panels, solar cell substrates, optical waveguides, light-guiding panels, and holographic memories.

EXAMPLES

The present invention will be illustrated in further detail with reference to several examples below. It should be noted, however, these are never construed to limit the scope of the present invention.

[Methods for Determining Properties and Methods for Evaluating Effects]

(1) Gas Chromatography (GC) Analysis of Bicyclohexyl-3,3'-diene and Isomers Thereof Measuring instrument: HP 6890 (supplied by Hewlett-Packard Company)

Column: HP-5, 60 m in length, 0.32 mm in inner diameter

Liquid phase: 5%-diphenyl-95%-dimethylpolysiloxane

Carrier gas: Nitrogen

Carrier gas flow rate: 2.6 ml/minute

Detector: FID

Inlet temperature: 250° C.

Detector temperature: 250° C.

Temperature rise pattern (column): Holding at 60° C. for 5 minutes, and heating to 300° C. at a rate of 10° C./minute Split ratio: 100
Sample: 1 μl The ratio between bicyclohexyl-3,3'-diene and isomers thereof was determined in the following manner. Specifically, gas chromatography was conducted under the above conditions, and the content ratio of the isomers to bicyclohexyl-3,3'-diene was determined based on the area of a maximum peak (bicyclohexyl-3,3'-diene) appearing at a retention time of around 20.97 minutes and the area of peaks (isomers) appearing at a retention time of around 20.91 minutes immediately prior to the maximum peak. Specifically, the isomer percentage (%) is calculated according to the formula: (Area of isomers)/[(Area of isomers)+(Area of bicyclohexyl-3,3'-diene)]×100

(2) Gas Chromatography (GC) Analysis of 3,4,3',4'-Diepoxybicyclohexyl and Isomers Thereof Measuring instrument: HP 6890 (supplied by Hewlett-Packard Company)
    Column: HP-5, 30 m in length, 0.25 μm in membrane thickness, 0.32 mm in inner diameter
    Liquid phase: 5%-diphenyl-95%-dimethylpolysiloxane
    Carrier gas: Nitrogen
    Carrier gas flow rate: 1.0 ml/minute
    Detector: FID
    Inlet temperature: 250° C.
    Detector temperature: 300° C.
    Temperature rise pattern (column): Holding at 100° C. for 2 minutes, heating to 300° C. at a rate of 5° C./minute, and holding at 300° C. for 10 minutes
    Split ratio: 100
    Sample: 1 μl (epoxy compound:acetone=1:40)

The ratio between 3,4,3',4'-diepoxybicyclohexyl and isomers thereof was determined in the following manner. Specifically, gas chromatography was conducted under the above conditions, and the content ratio of the isomers to 3,4,3',4'-diepoxybicyclohexyl was determined based on the total area of two maximum peaks appearing at retention times of from around 19.8 minutes to around 20.0 minutes and the total area of three peaks appearing at retention times of from around 19.1 minutes to around 19.5 minutes immediately prior to the maximum peaks. The two maximum peaks were two (major) peaks having longest retention times [3,4,3',4'-diepoxybicyclohexyl] in peaks of compounds having an identical molecular weight. The two major peaks were appeared because isomers having different steric positional relations of an oxirane oxygen bonded to one cyclohexane ring with the other cyclohexane ring were presented. The three peaks appearing immediately prior to the maximum peaks were peaks other than the two major peaks having the longest retention times in peaks of compounds having an identical molecular weight. Specifically, the isomer percentage (%) is calculated according to the formula: (Total area of isomers)/[(Total area of isomers)+(Total area of 3,4,3',4'-diepoxybicyclohexyl)]×100

(3) Gas Chromatography-Mass Spectrometry (GC-MS) Analysis of 3,4,3',4'-Diepoxybicyclohexyl and Isomers Thereof Measuring instrument: HP 6890 (GC unit) and HP 5973 (MS unit) each supplied by Hewlett-Packard Company
    Column: HP-5MS, 30 m in length, 0.25 μm in membrane thickness, 0.25 mm in inner diameter
    Liquid phase: 5%-diphenyl-95%-dimethylpolysiloxane
    Temperature rise pattern (column): Holding at 100° C. for 2 minutes, heating to 300° C. at a rate of 5° C./minute, and holding at 300° C. for 18 minutes
    Inlet temperature: 250° C.
    MSD transfer line temperature: 280° C.
    Carrier gas: Helium
    Carrier gas flow rate: 0.7 ml/minute (constant flow)
    Split ratio: Split-less
    Sample amount: 1.0 μl
    Measurement mode: Electron ionization (EI)
    Ion source temperature: 230° C.
    Quadrupole temperature: 106° C.
    Mass spectrometry range: m/z=25-400
    Sample preparation: Sample (0.1 g) is dissolved in acetone (3.0 g)

Figure 6:
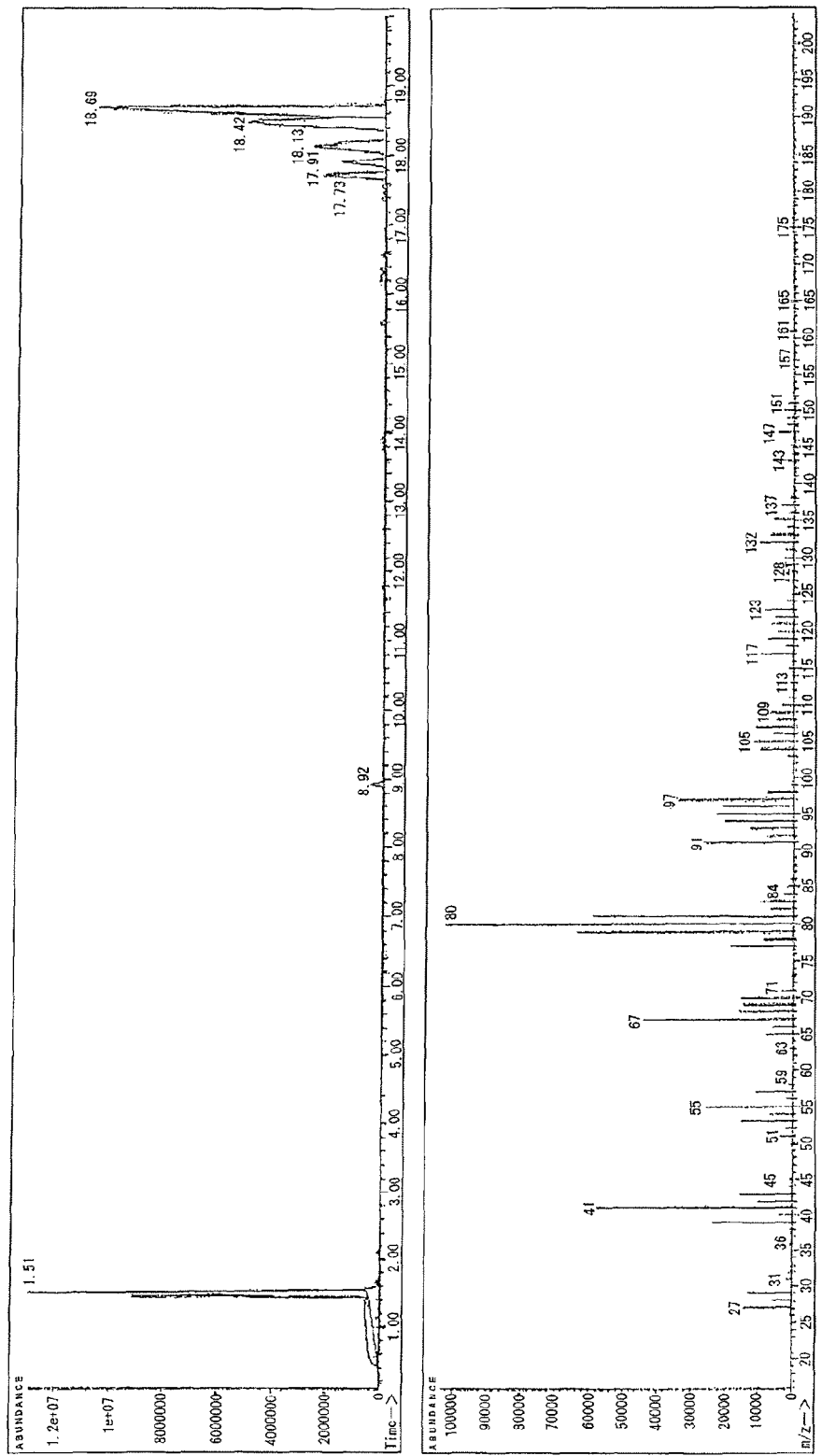
FIG. 6 depicts a gas chromatogram (total ion chromatogram) (upper diagram) and a MS spectrum of a peak at a retention time of 17.73 minutes (lower diagram), respectively, as determined in gas chromatography-mass spectrometry (GC-MS) of the alicyclic diepoxy compound prepared according to Preparation Example 1.
Figure 7:
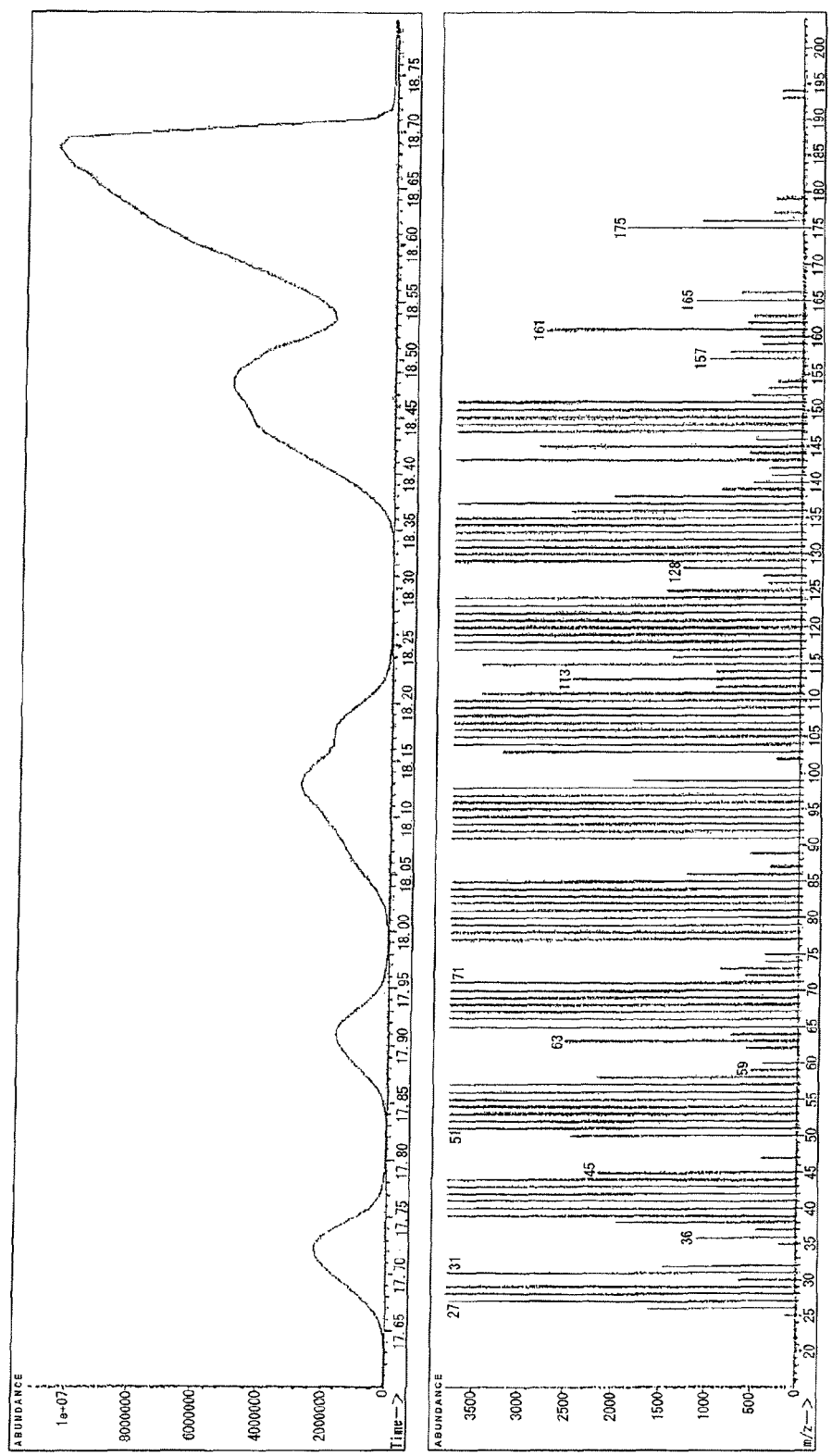
FIG. 7 depicts an enlarged view of the gas chromatogram (total ion chromatogram) (upper diagram) and an enlarged view of the MS spectrum of the peak at a retention time of 17.73 minutes (lower diagram), respectively, as determined in gas chromatography-mass spectrometry (GC-MS) of the alicyclic diepoxy compound prepared according to Preparation Example 1.
Figure 8:
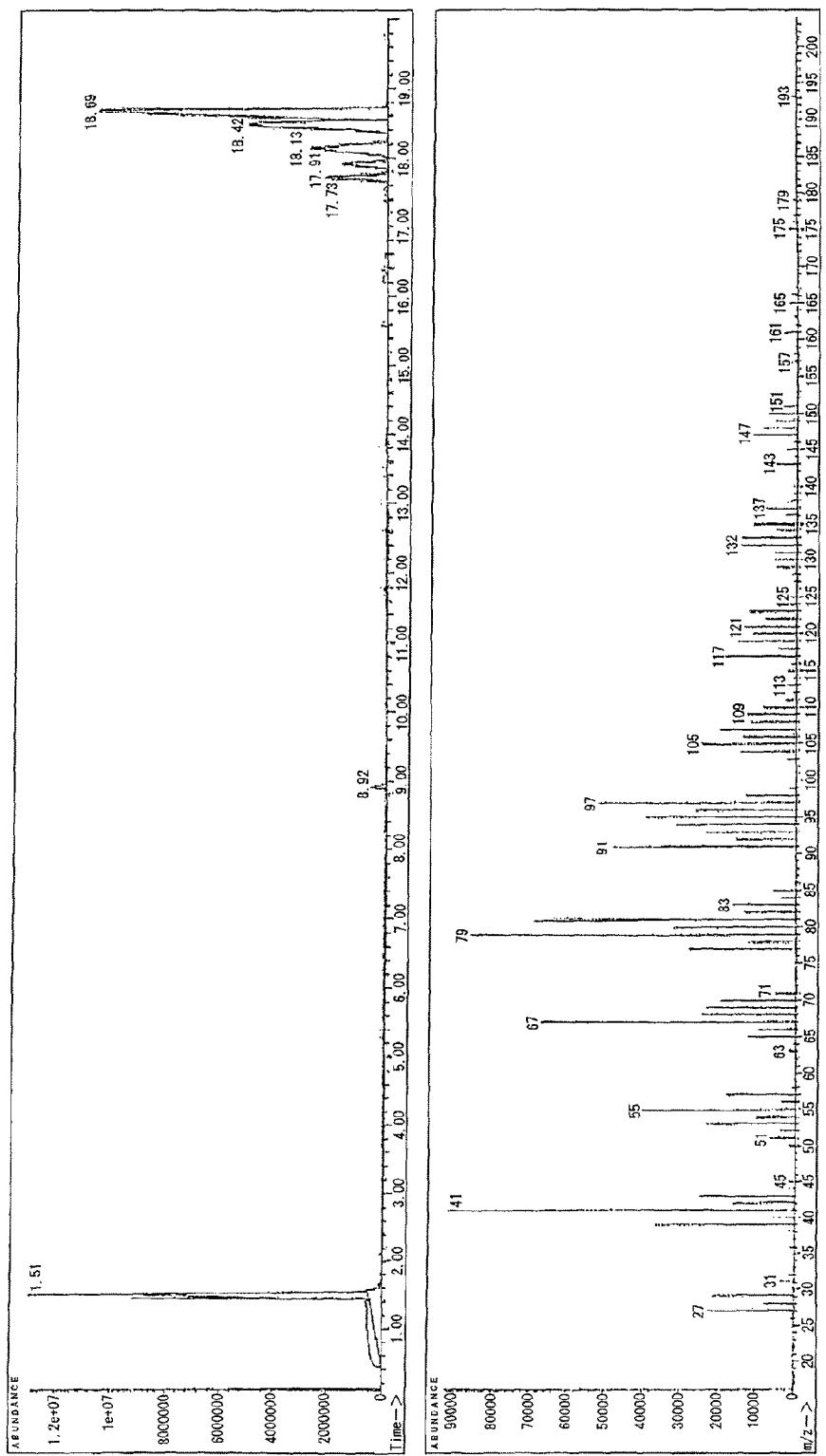
FIG. 8 depicts a gas chromatogram (total ion chromatogram) (upper diagram) and a MS spectrum of a peak at a retention time of 17.91 minutes (lower diagram), respectively, as determined in gas chromatography-mass spectrometry (GC-MS) of the alicyclic diepoxy compound prepared according to Preparation Example 1.
Figure 9:
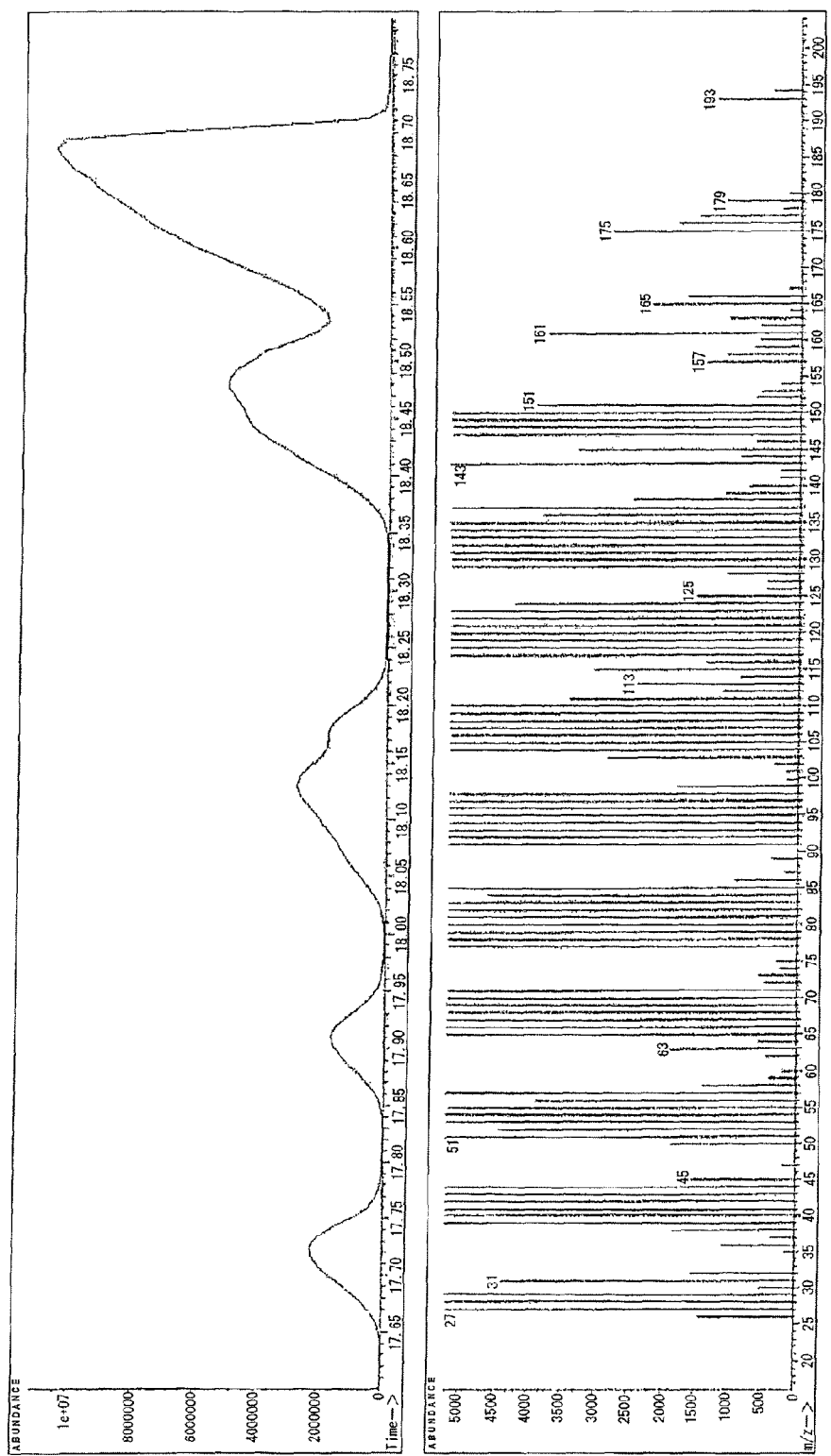
FIG. 9 depicts an enlarged view of the gas chromatogram (total ion chromatogram) (upper diagram) and an enlarged view of the MS spectrum of the peak at a retention time of 17.91 minutes (lower diagram), respectively, as determined in gas chromatography-mass spectrometry (GC-MS) of the alicyclic diepoxy compound prepared according to Preparation Example 1.
Figure 10:
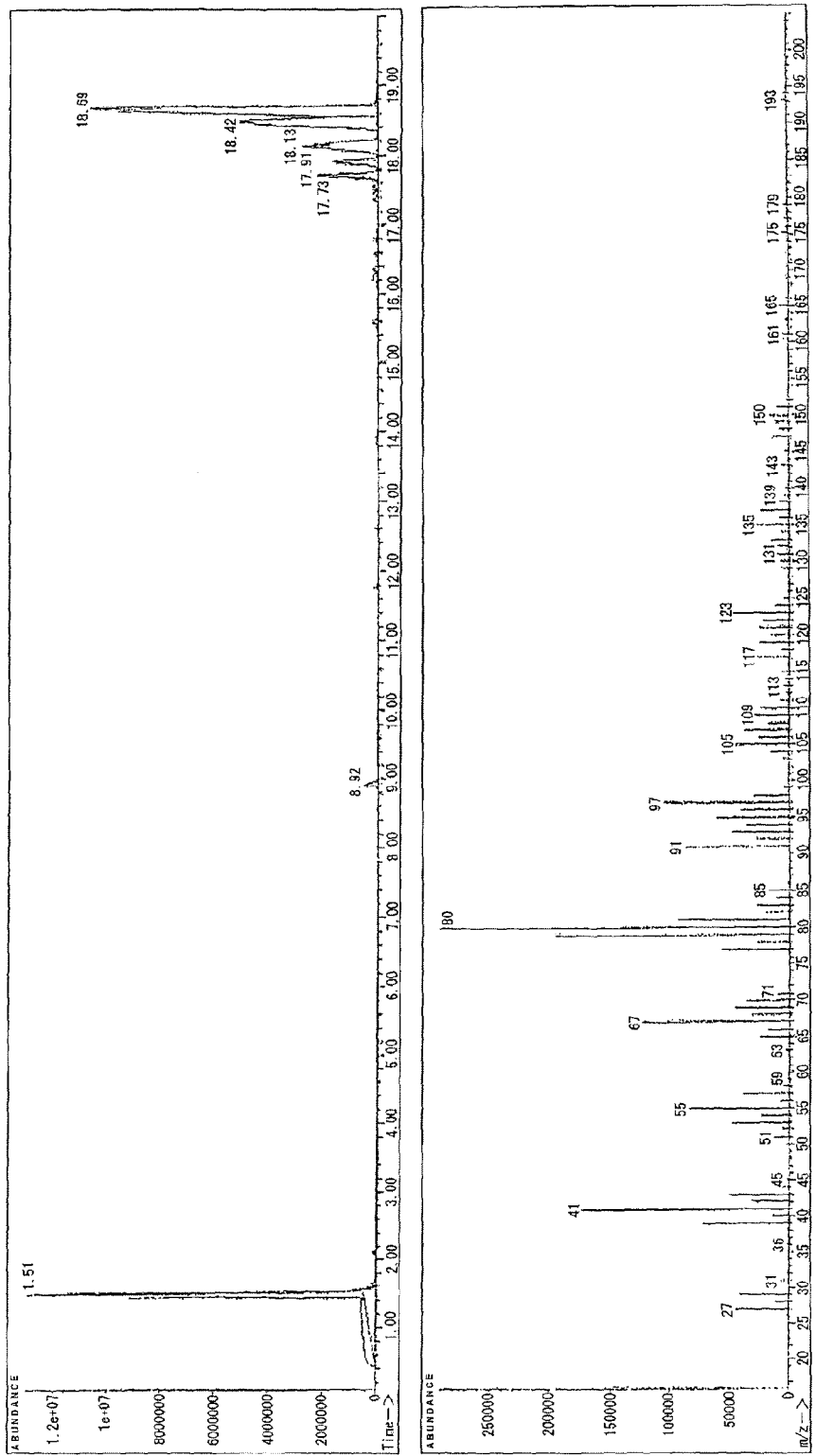
FIG. 10 depicts a gas chromatogram (total ion chromatogram) (upper diagram) and a MS spectrum of a peak at a retention time of 18.13 minutes (lower diagram), respectively, as determined in gas chromatography-mass spectrometry (GC-MS) of the alicyclic diepoxy compound prepared according to Preparation Example 1.
Figure 11:
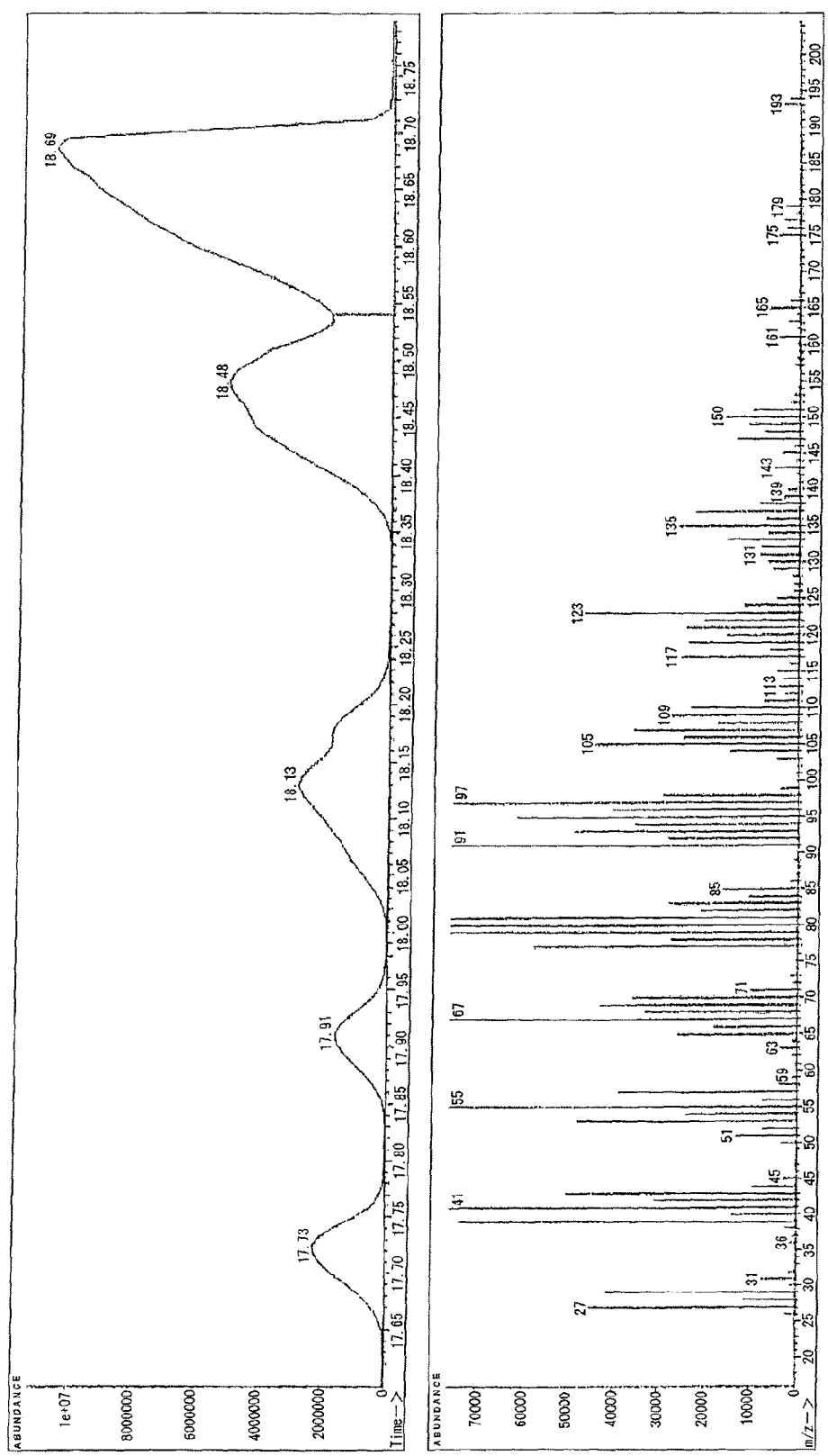
FIG. 11 depicts an enlarged view of the gas chromatogram (total ion chromatogram) (upper diagram) and an enlarged view of the MS spectrum of the peak at a retention time of 18.13 minutes (lower diagram), respectively, as determined in gas chromatography-mass spectrometry (GC-MS) of the alicyclic diepoxy compound prepared according to Preparation Example 1.
Figure 12:
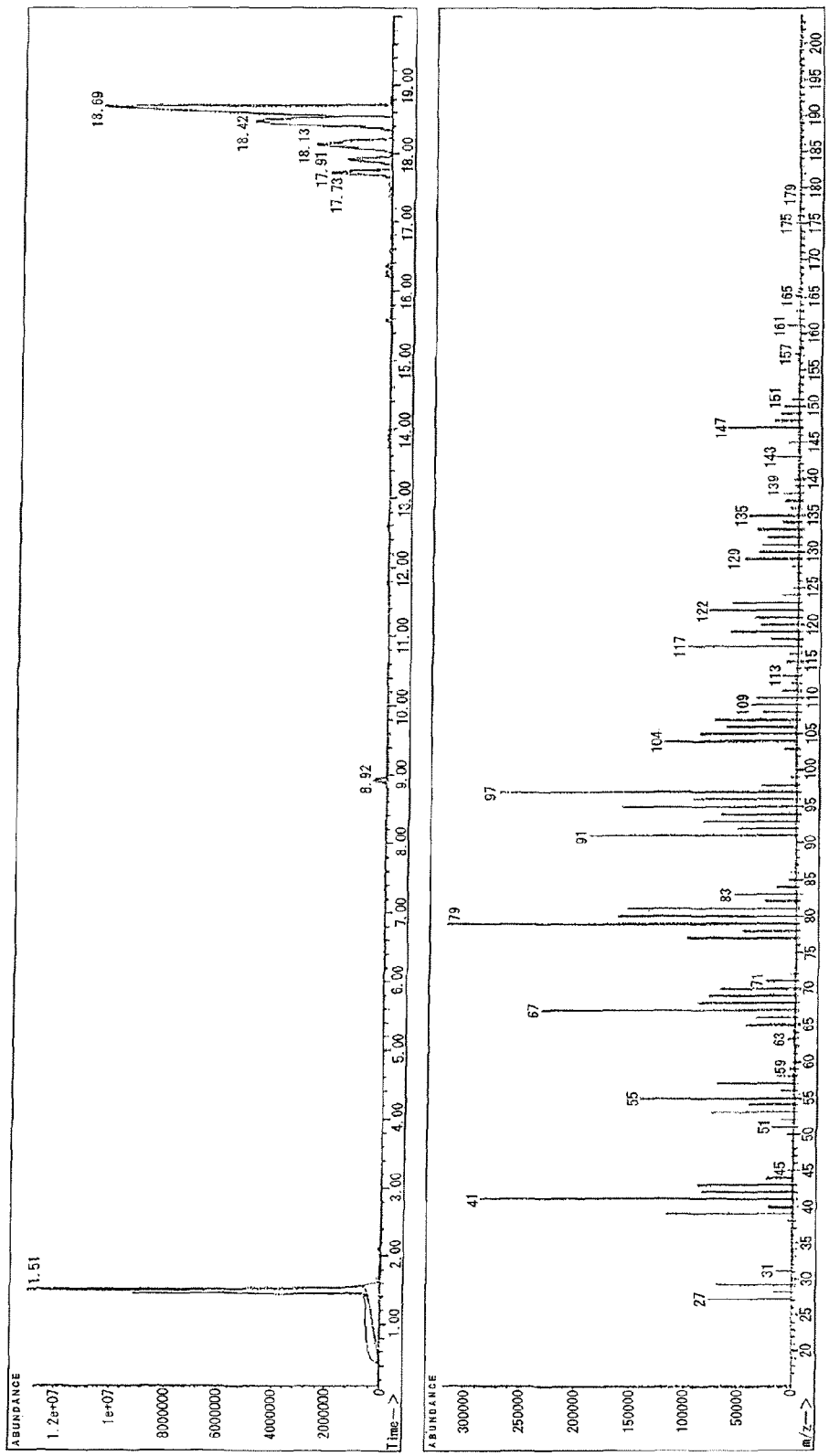
FIG. 12 depicts a gas chromatogram (total ion chromatogram) (upper diagram) and a MS spectrum of a peak at a retention time of 18.48 minutes (lower diagram), respectively, as determined in gas chromatography-mass spectrometry (GC-MS) of the alicyclic diepoxy compound prepared according to Preparation Example 1.
Figure 13:
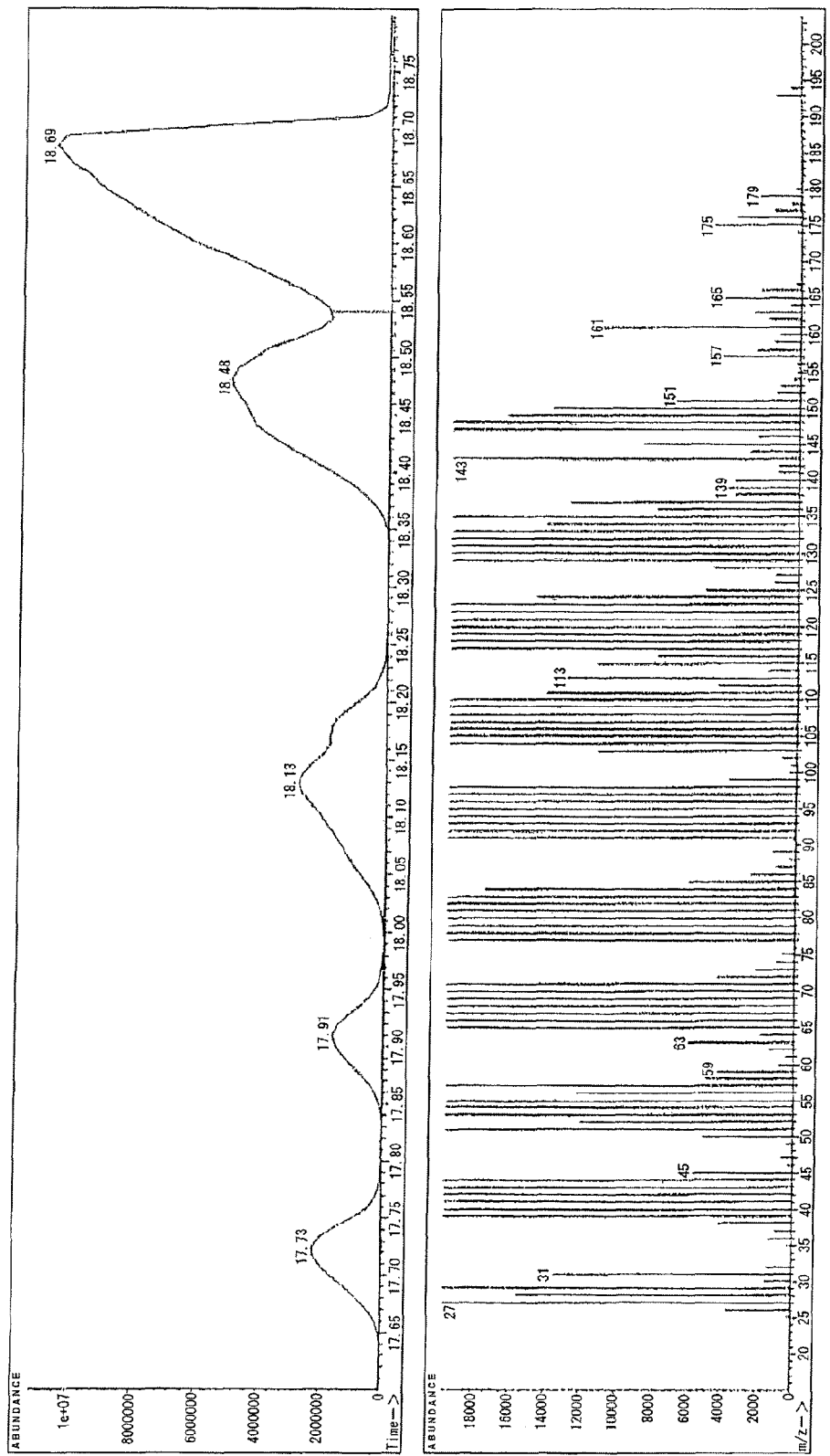
FIG. 13 depicts an enlarged view of the gas chromatogram (total ion chromatogram) (upper diagram) and an enlarged view of the MS spectrum of the peak at a retention time of 18.48 minutes (lower diagram), respectively, as determined in gas chromatography-mass spectrometry (GC-MS) of the alicyclic diepoxy compound prepared according to Preparation Example 1.
Figure 14:
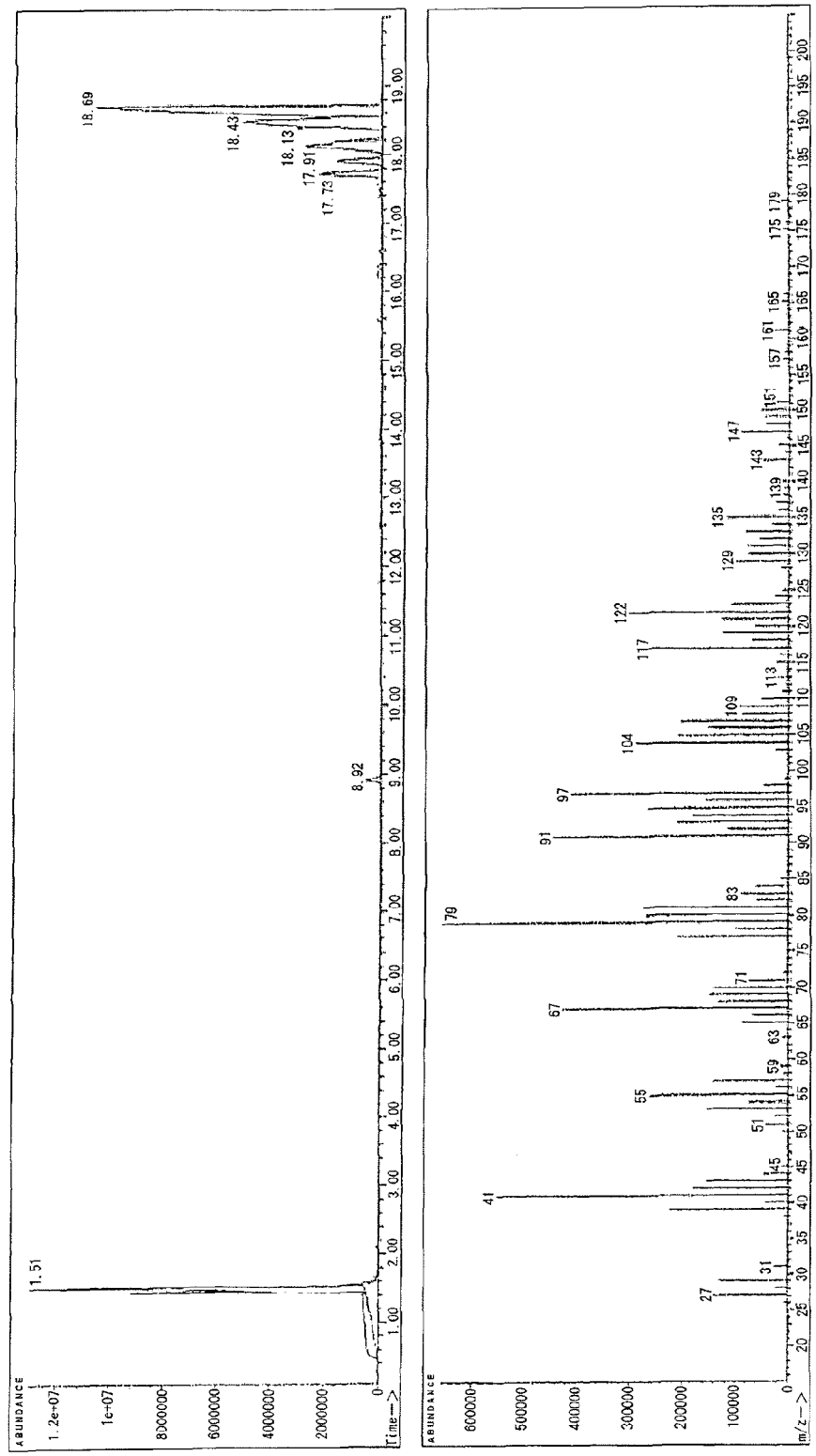
FIG. 14 depicts a gas chromatogram (total ion chromatogram) (upper diagram) and a MS spectrum of a peak at a retention time of 18.69 minutes (lower diagram), respectively, as determined in gas chromatography-mass spectrometry (GC-MS) of the alicyclic diepoxy compound prepared according to Preparation Example 1.
Figure 15:
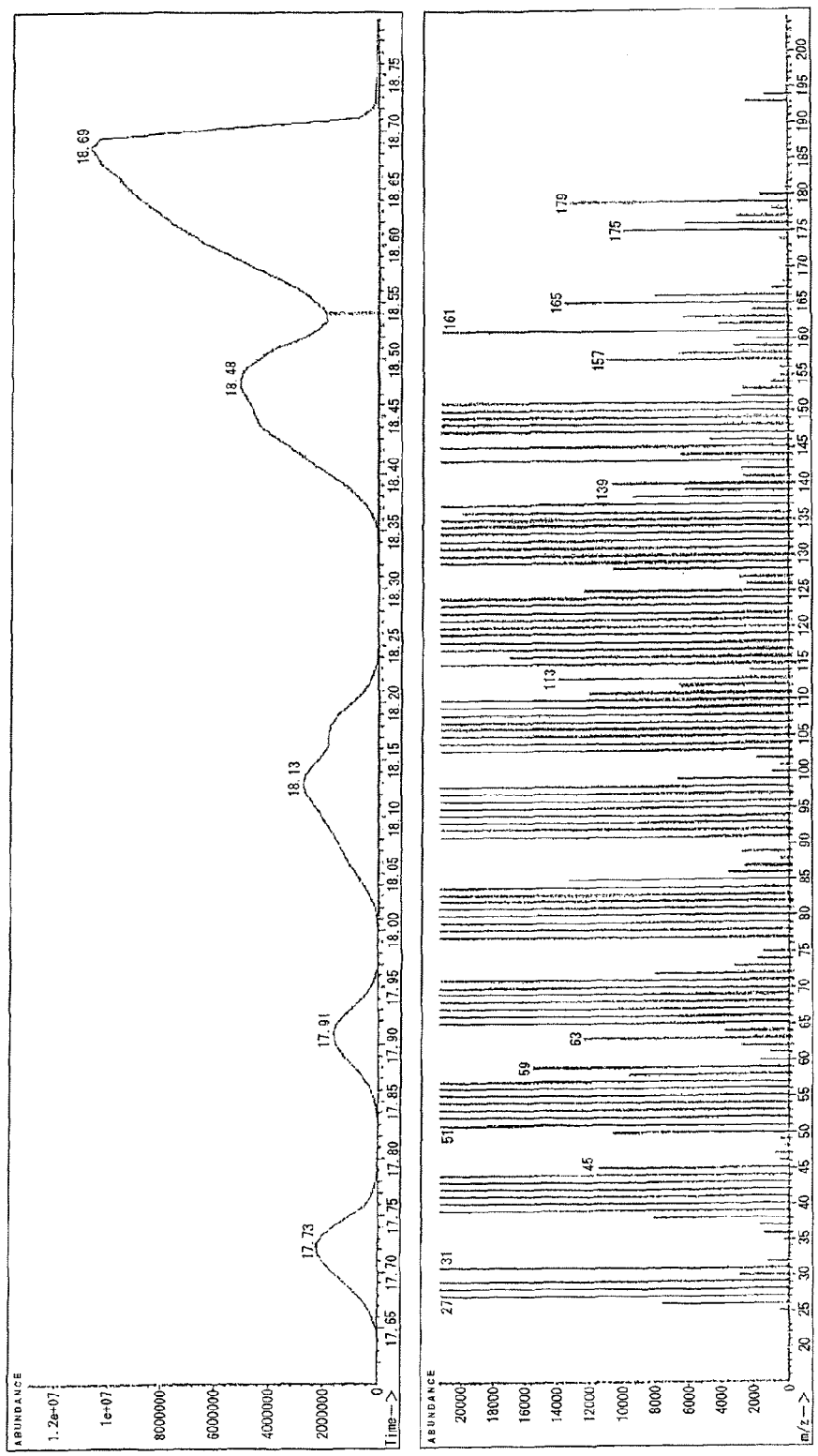
FIG. 15 depicts an enlarged view of the gas chromatogram (total ion chromatogram) (upper diagram) and an enlarged view of the MS spectrum of the peak at a retention time of 18.69 minutes (lower diagram), respectively, as determined in gas chromatography-mass spectrometry (GC-MS) of the alicyclic diepoxy compound prepared according to Preparation Example 1.

An alicyclic diepoxy compound prepared according to Preparation Example 1 was subjected to gas chromatography-mass spectrometry (GC-MS). The results [gas chromatograms (total ion chromatograms) and MS spectra of respective components] are shown in FIGS. 6 to 15. Peaks at retention times of 17.73 minutes, 17.91 minutes, and 18.13 minutes are peaks derived from isomers of 3,4,3',4'-diepoxybicyclohexyl; and peaks at retention times of 18.48 minutes and 18.69 minutes are peaks derived from 3,4,3',4'-diepoxybicyclohexyl. Since analyses were conducted under conditions somewhat differing from those in the gas chromatography, the respective peaks appear at different retention times but appear in the same order as in the gas chromatography. FIG. 6 depicts a gas chromatogram (total ion chromatogram) and a MS spectrum of a peak at a retention time of 17.73 minutes, and FIG. 7 depicts enlarged views thereof. FIG. 8 depicts the gas chromatogram (total ion chromatogram) and a MS spectrum of a peak at a retention time of 17.91 minutes, and FIG. 9 depicts enlarged views thereof. FIG. 10 depicts the gas chromatogram (total ion chromatogram) and a MS spectrum of a peak at a retention time of 18.13 minutes, and FIG. 11 depicts enlarged views thereof. FIG. 12 depicts the gas chromatogram (total ion chromatogram) and a MS spectrum of a peak at a retention time of 18.48 minutes, and FIG. 13 depicts enlarged views thereof. FIG. 14 depicts the gas chromatogram (total ion chromatogram) and a MS spectrum of a peak at a retention time of 18.69 minutes, and FIG. 15 depicts enlarged views thereof. The MS spectra demonstrate that all the components have a molecular ion peak at m/z of 194.

(4) Thermal Stability Test of Thermally Cured Article

Samples were prepared by subjecting curable compositions, prepared according to Examples 1 to 3 and Comparative Example 1 in Table 2, to primary curing at 45° C. for two hours and thereafter to secondary curing at 150° C. for one hour. The cured articles were measured on glass transition point Tg (° C.) through thermo-mechanical analysis (TMA) under a condition of a temperature elevation rate of 5° C./minute. A measuring instrument used herein was "TMA/SS6000" (supplied by Seiko Instruments Inc.). In order to obtain "coefficient of linear expansion", dimensional changes from 50° C. to 200° C. were measured in thermo-mechanical analysis at a temperature elevation rate of 5° C./minute, and the average of measured dimensional changes was defined as the coefficient of linear expansion. For "appearance at 300° C.", the sample piece upon heating to 300° C. was recovered, and the external appearance of the sample piece was visually compared.

(5) Glass Transition Temperature (Tg) of Ultraviolet (UV)-Cured Articles

Curable compositions prepared according to Examples 4 to 6 and Comparative Example 2 in Table 3 were respectively applied to a steel sheet using an applicator, to give coats each 20 μm thick. The coats were cured by applying an ultraviolet ray at an integrated light quantity of 500 mJ/cm$^2$ through an ultraviolet irradiator (supplied by Eye Graphics Co., Ltd. under the trade name of "ECS-401GX"), post-cured at 80° C. for one hour, and thereby yielded test pieces. The test pieces were measured at temperatures from 30° C. to 300° C. with a rigid-body pendulum type viscoelasticity measuring instrument (supplied by A&D Co., Ltd. under the trade name of "RPT 3000") equipped with a cylindrical edge having 4 mm of diameter. Of two more peaks observed at different temperatures in logarithmic decrement, a peak observed at the lowest temperature in logarithmic decrement was selected, and the temperature thereof was defined as a glass transition temperature (Tg).

(6) Thermal Stability Test of Cured Articles Using Curing Agent

Samples were prepared by subjecting curable compositions, prepared according to Examples 7 to 8 and Comparative Example 3 in Table 4, to primary curing at 100° C. for three hours, and thereafter to secondary curing at 150° C. for three hours. These cured articles were measured on glass transition point Tg (° C.) through thermo-mechanical analysis (TMA) measured at a temperature elevation rate of 5° C./minute. A measuring instrument used herein was "TMA/SS6000" (supplied by Seiko Instruments Inc.). In order to obtain "coefficient of linear expansion", dimensional changes from 50° C. to 200° C. were measured in thermo-mechanical analysis at a temperature elevation rate of 5° C./minute, and the average of measured dimensional changes was defined as the coefficient of linear expansion. As "appearance at 300° C.", the sample piece upon heating to 300° C. was recovered, and the external appearance of the sample piece was visually compared.

Preparation Example 1

Isomer Percentage: 9%

A dehydration catalyst was prepared by mixing and stirring 70 g (0.68 mol) of 95 percent by weight sulfuric acid with 55 g (0.36 mol) of 1,8-diazabicyclo[5.4.0]undecene-7 (DBU).

In a 3-liter flask equipped with a stirrer, a thermometer, and a distillation line provided with a water outlet and kept at a constant temperature, were placed 1000 g (5.05 mol) of hydrogenated biphenol (i.e., 4,4'-dihydroxybicyclohexyl) represented by following Formula (3a):

[Chemical Formula 4]

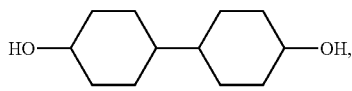

(3a)

125 g (0.68 mol in terms of sulfuric acid) of the above-prepared dehydration catalyst, and 1500 g of pseudocumene, and the flask was heated. Formation of water was detected around the time when the inner temperature became higher than 115° C. The heating was further continued until the temperature reached the boiling point of pseudocumene (inner temperature: 162° C. to 170° C.), to carry out dehydration under normal pressure. By-product water was distilled out and discharged out of the system via the water outlet. Under the reaction conditions, the dehydration catalyst was liquid and finely dispersed in the reaction liquid. After a lapse of three hours, a substantially theoretical amount of water (180 g) was distilled, whereby the reaction was deemed to complete. Using a 10-tray Oldershaw distillation column, pseudocumene was distilled off from the reaction mixture after the completion of the reaction, and the residue was further subjected to distillation at an inner temperature of 137° C. to 140° C. and an inner pressure of 10 Torr (1.33 kPa), to thereby yield 731 g of bicyclohexyl-3,3'-diene. A result of gas chromatography analysis showed the fact that the prepared bicyclohexyl-3,3'-diene contained isomers thereof (the fact was also confirmed by gas chromatography-mass spectrometry (GC-MS) analysis), and the content ratio of bicyclohexyl-3,3'-diene represented by following Formula (2a):

[Chemical Formula 5]

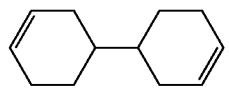

Figure 5:
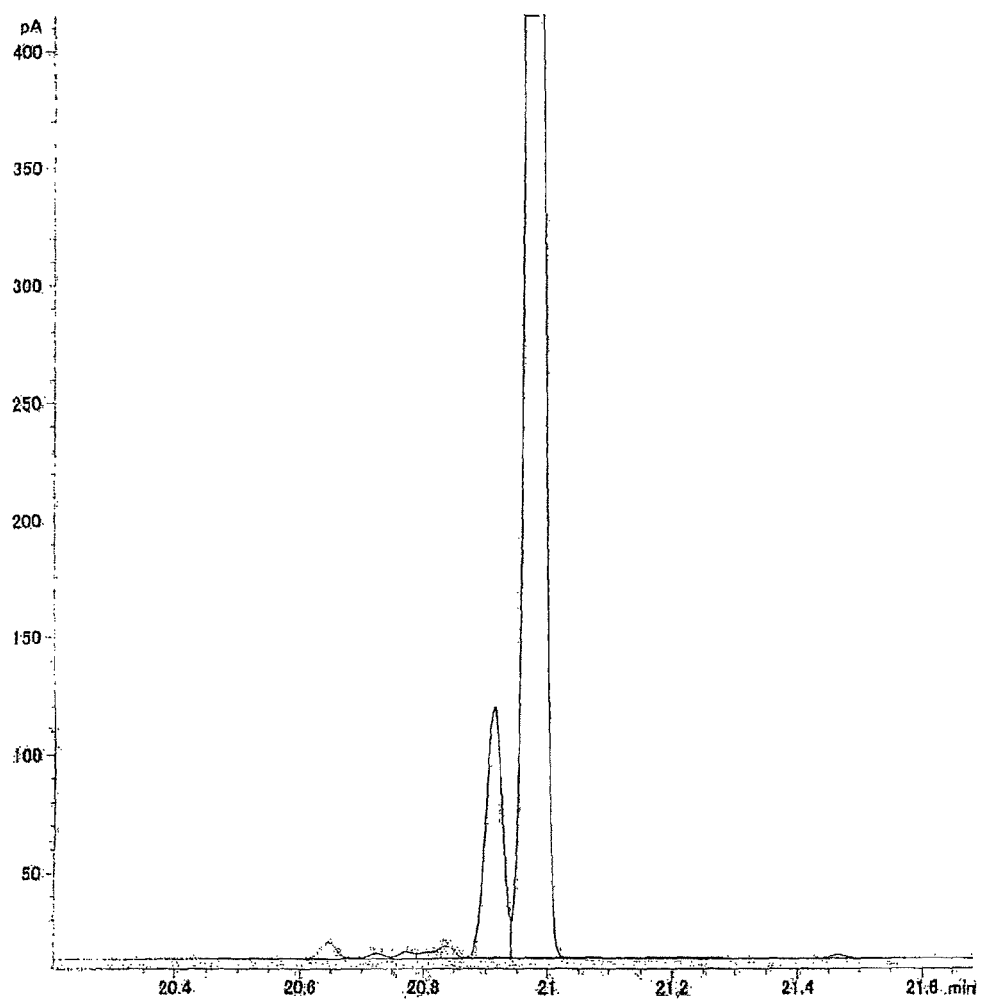
FIG. 5 depicts a gas chromatographic chart of a bicyclohexyl-3,3'-diene prepared according to Preparation Example 1.

(2a)

to the isomers thereof was 91:9, as determined by gas chromatography (see FIG. 5).

In a reactor were placed 243 g of the prepared bicyclohexyl-3,3'-diene (inclusive of its isomers) and 730 g of ethyl acetate. Thereafter, 274 g of a 30 percent by weight solution of peroxyacetic acid in ethyl acetate (water content: 0.41 percent by weight) was added dropwise in the reactor over three hours while blowing nitrogen gas into the gas phase and controlling the inner temperature of the reaction system to 37.5° C. After the completion of dropwise addition of the peroxyacetic acid solution, aging was conducted at 40° C. for one hour, whereby the reaction was completed. The crude reaction mixture upon the completion of reaction was washed with water at 30° C., and low-boiling compounds were removed from the washed reaction mixture at a temperature of 70° C. and a pressure of 20 mmHg to give 270 g of an alicyclic epoxy compound in a yield of 93%. This compound was found to have a viscosity (25° C.) of 84 mPa·s. The prepared alicyclic epoxy compound had an oxirane oxygen concentration of 15.0 percent by weight. The 1H-NMR measurement of the alicyclic epoxy compound showed that a peak derived from an internal double bond and appearing at δ of around 4.5 to 5 ppm disappeared, and a peak of proton derived from epoxy group appeared at δ of around 3.1 ppm, to find that the compound was 3,4,3',4'-diepoxybicyclohexyl represented by following Formula (1a):

[Chemical Formula 6]

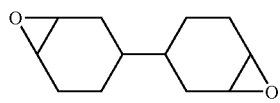

(1a)

The prepared alicyclic epoxy compound was found to contain 3,4,3',4'-diepoxybicyclohexyl and isomers thereof and have an isomer percentage of 9%, as determined by gas chromatography (see FIG. 1). The isomer percentage was calculated according to the following equation:

Isomer percentage=(2262+1715+5702)/(2262+1715+5702+28514+74587)×100=9%

Preparation Example 2

Isomer Percentage: 14%

In a 3-liter flask equipped with a stirrer, a thermometer, and a distillation line provided with a water outlet and kept at a constant temperature, were placed 840 g (4.24 mol) of hydrogenated biphenol, 170 g (1.73 mol) of phosphoric acid, and 2350 g of undecane, and the flask was heated. Formation of water was detected from around the time when the inner temperature became higher than 110° C. The heating was further continued until the temperature reached the boiling point of undecane (inner temperature: 189° C. to 194° C.), and dehydration was conducted under normal pressure. By-product water was distilled off and discharged from the system via the water outlet. In this process, p-toluenesulfonic acid was fully dissolved in the reaction liquid under the reaction conditions. After a lapse of five and a half hours, a substantially theoretical amount of water (150 g) was distilled out, whereby the reaction was deemed to complete. Using a 10-tray Oldershaw distillation column, undecane was distilled off from the resulting reaction mixture, and the residue was further subjected to distillation at an inner temperature of 138° C. to 141° C. and an inner pressure of 10 Torr (1.33 kPa) and thereby yielded 474.2 g of bicyclohexyl-3,3'-diene. The prepared bicyclohexyl-3,3'-diene contained isomers with a content ratio of bicyclohexyl-3,3'-diene to the isomers of 87:13, as determined by gas chromatography.

In a reactor were placed 243 g of the prepared bicyclohexyl-3,3'-diene (inclusive of its isomers) and 730 g of ethyl acetate, and 274 g of a 30 percent by weight solution of peroxyacetic acid in ethyl acetate (water content: 0.41 percent by weight) was added dropwise in the reactor over three hours while blowing nitrogen gas into the gas phase and controlling the inner temperature of the reaction system to 37.5° C. After the completion of dropwise addition of the peroxyacetic acid solution, aging was conducted at 40° C. for one hour, whereby the reaction was completed. The crude reaction mixture upon the completion of reaction was washed with water at 30° C., and low-boiling compounds were removed from the washed reaction mixture at a temperature of 70° C. and a pressure of 20 mmHg to yield 261 g of an alicyclic epoxy compound in a yield of 90%. This compound was found to have a viscosity (25° C.) of 75 mPa·s. The prepared alicyclic epoxy compound had an oxirane oxygen concentration of 15.0 percent by weight. The 1H-NMR measurement of the alicyclic epoxy compound showed that a peak derived from an internal double bond and appearing at δ of around 4.5 to 5 ppm disappeared and a peak of proton derived from epoxy group appeared at δ of around 3.1 ppm, to find that the compound is 3,4,3',4'-diepoxybicyclohexyl. The prepared alicyclic epoxy compound was found to contain 3,4,3',4'-diepoxybicyclohexyl and isomers thereof and to have an isomer percentage of 14%, as determined by gas chromatography (see FIG. 2). The isomer percentage was calculated according to the following equation:

Isomer percentage=(2821+2108+6988)/(2821+2108+ 6988+20792+54602)×100=14%

Preparation Example 3

Isomer Percentage: 17%

In a 5-liter flask equipped with a stirrer, a 20-tray Oldershaw distillation column, and a thermometer were placed 1000 g (5.05 mol) of hydrogenated biphenol, 40 g (0.265 mol) of ammonium hydrogen sulfate, and 2800 g of cumene, and the flask was heated. Formation of water was detected from around the time when the inner temperature became higher than 115° C. The heating was further continued and the reaction was continued to raise the temperature to the boiling point of cumene (inner temperature: 165° C. to 170° C.), and dehydration was conducted under normal pressure while by-product water was distilled out as an overhead from the distillation column. In this process, ammonium hydrogen sulfate was solid and most thereof was not dissolved in the reaction liquid under the reaction conditions. After a lapse of six and a half hours, 94% of the theoretical amount of water (170.9 g) was distilled out, whereby the reaction was deemed to complete. After the completion of reaction, cumene was distilled off under reduced pressure, and the system was further evacuated to a pressure of 10 Torr (1.33 kPa), followed by distillation at an inner temperature of 137° C. to 141° C., to yield 590 g of bicyclohexyl-3,3'-diene. The prepared bicyclohexyl-3,3'-diene was found to contain isomers and to have a content ratio of bicyclohexyl-3,3'-diene to the isomers of 81:19, as determined by gas chromatography.

In a reactor, 243 g of the prepared bicyclohexyl-3,3'-diene (inclusive of its isomers) and 730 g of ethyl acetate were placed. Thereafter, 274 g of a 30 percent by weight solution of peroxyacetic acid in ethyl acetate (water content: 0.41 percent by weight) was added dropwise in the reactor over three hours while blowing nitrogen gas into the gas phase and controlling the inner temperature of the reaction system to 37.5° C. After the completion of dropwise addition of the peroxyacetic acid solution, aging was conducted at 40° C. for one hour, whereby the reaction was completed. The crude reaction mixture upon the completion of reaction was washed with water at 30° C., and low-boiling compounds were removed from the washed reaction mixture at a temperature of 70° C. and a pressure of 20 mmHg, to give 269 g of an alicyclic epoxy compound in a yield of 92%. This compound was found to have a viscosity (25° C.) of 69 mPa·s. The prepared alicyclic epoxy compound had an oxirane oxygen concentration of 14.9 percent by weight. The 1H-NMR measurement of the alicyclic epoxy compound showed that a peak derived from an internal double bond and appearing at δ of around 4.5 to 5 ppm disappeared and a peak of proton derived from epoxy group appeared at δ of around 3.1 ppm, to find that the compound is 3,4,3',4'-diepoxybicyclohexyl. The prepared alicyclic epoxy compound was found to contain 3,4,3',4'-diepoxybicyclohexyl and isomers thereof and have an isomer percentage of 17%, as determined by gas chromatography (see FIG. 3). The isomer percentage was calculated according to the following equation:

Isomer percentage=(3668+2724+9033)/(3668+2724+ 9033+20413+53424)×100=17%

Comparative Preparation Example 1

In a 10-liter four-necked flask equipped with a stirrer, a 20-tray distillation column, and a thermometer were placed 6 kg of hydrogenated biphenol and 620 g of potassium hydrogen sulfate. Next, the flask was heated to 180° C. to melt the hydrogenated biphenol, followed by stirring. The reaction was continued while by-product water was distilled out as an overhead from the distillation column. After a lapse of three hours, the reaction system was evacuated to a pressure of 10 Torr (1.33 kPa), and water and bicyclohexyl-3,3'-diene were continuously distilled out of the system from the uppermost tray of the distillation column. The water and bicyclohexyl-3,3'-diene distilled out of the system were separated into two layers in a decanter, and the upper layer alone was recovered. Thereafter, the reaction temperature was raised to 220° C. over four hours, and the reaction was deemed to complete at the time when distillation of water and bicyclohexyl-3,3'-diene was ceased. A crude distillate of bicyclohexyl-3,3'-diene was obtained in a yield of 4507 g. In a 5-liter four-necked flask equipped with a stirrer, a 20-tray distillation column, and a thermometer was placed 4500 g of the crude distillate of bicyclohexyl-3,3'-diene, and the temperature of the flask was raised to 180° C. on an oil bath. The reaction system was then evacuated to a pressure of 10 Torr (1.33 kPa) to distil off water, thereafter bicyclohexyl-3,3'-diene was purified by distillation over five hours at a reflux ratio of 1, while keeping the temperature of the uppermost tray of the distillation column at 145° C., to thereby yield 4353 g of a colorless transparent liquid. The liquid was analyzed by gas chromatography to find that the prepared bicyclohexyl-3,3'-diene contains isomers and a content ratio of the bicyclohexyl-3,3'-diene to the isomers was 80:20.

In a reactor were placed 243 g of the prepared bicyclohexyl-3,3'-diene (inclusive of its isomers) and 730 g of ethyl acetate. Thereafter, 274 g of a 30 percent by weight solution of peroxyacetic acid in ethyl acetate (water content: 0.41 percent by weight) was added dropwise over three hours while blowing nitrogen gas into the gas phase and controlling the inner temperature of the reaction system to 37.5° C. After the completion of dropwise addition of the peroxyacetic acid solution, aging was conducted at 40° C. for one hour, whereby the reaction was completed. The crude reaction mixture upon the completion of reaction was washed with water at 30° C., from which low-boiling compounds were removed at a temperature of 70° C. and a pressure of 20 mmHg, to give 267 g of an alicyclic epoxy compound in a yield of 92%. This compound was found to have a viscosity (25° C.) of 63 mPa·s. The prepared alicyclic epoxy compound had an oxirane oxygen concentration of 14.9 percent by weight. The 1H-NMR measurement of the alicyclic epoxy compound showed that a peak derived from an internal double bond and appearing at δ of around 4.5 to 5 ppm disappeared and a peak of proton derived from epoxy group appeared at δ of around 3.1 ppm, to find that the compound is 3,4,3',4'-diepoxybicyclohexyl. The prepared alicyclic epoxy compound was found to contain 3,4,3',4'-diepoxybicyclohexyl and isomers thereof and have an isomer percentage of 21%, as determined by gas chromatography (see FIG. 4). The isomer percentage was calculated according to the following equation:

Isomer percentage=(5404+3923+13067)/(5404+ 3923+13067+23563+60859)×100=21%

Example 1

A curable composition was prepared by mixing 100 parts by weight of the alicyclic epoxy compound prepared according to Preparation Example 1 with 0.3 part by weight of "San-Aid SI-60L" (a sulfonium salt cationic polymerization initiator) supplied by Sanshin Chemical Industry Co., Ltd. A sample was prepared by subjecting the curable composition to primary curing at 45° C. for two hours and thereafter to secondary curing at 150° C. for one hour. The glass transition temperature (Tg) of the sample cured article was measured through thermo-mechanical analysis (TMA) at a temperature elevation rate of 5° C./minute, but no inflection point, which indicates the glass transition temperature (Tg), was observed even at 340° C. The cured article had a coefficient of linear expansion of 63 ppm, as calculated from a dimensional change from 50° C. to 200° C. determined in the above thermo-mechanical analysis. The cured article showed a transparent appearance upon heating to 300° C. at a temperature elevation rate of 5° C./minute.

Example 2

A curable composition was prepared by mixing 100 parts by weight of the alicyclic epoxy compound prepared according to Preparation Example 2 with 0.3 part by weight of "San-Aid SI-60L" (a sulfonium salt cationic polymerization initiator) supplied by Sanshin Chemical Industry Co., Ltd. The curable composition was cured and properties of the cured article were evaluated by the procedure of Example 1. The glass transition temperature (Tg) of the sample cured article was measured, but no inflection point, which indicates the glass transition temperature (Tg), was observed even at 340° C. The cured article had a coefficient of linear expansion of 60 ppm and showed a transparent appearance upon heating to 300° C.

Example 3

A curable composition was prepared by mixing 100 parts by weight of the alicyclic epoxy compound prepared according to Preparation Example 3 with 0.3 part by weight of "San-Aid SI-60L" (a sulfonium salt cationic polymerization initiator) supplied by Sanshin Chemical Industry Co., Ltd. The curable composition was cured and properties of the cured article were evaluated by the procedure of Example 1. The glass transition temperature (Tg) of the sample cured article was measured, but no inflection point, which indicates the glass transition temperature (Tg), was observed even at 340° C. The cured article had a coefficient of linear expansion of 67 ppm and showed a transparent appearance upon heating to 300° C.

Comparative Example 1

A curable composition was prepared by mixing 100 parts by weight of the alicyclic epoxy compound prepared according to Comparative Preparation Example 1 with 0.3 part by weight of "San-Aid SI-60L" (a sulfonium salt cationic polymerization initiator) supplied by Sanshin Chemical Industry Co., Ltd. The curable composition was cured and properties of the cured article were evaluated by the procedure of Example 1. The cured article had a glass transition temperature (Tg) of 298° C., had a coefficient of linear expansion of 102 ppm, and showed a cloudy appearance upon heating to 300° C.

Example 4

100 parts by weight of the alicyclic epoxy compound prepared according to Preparation Example 1 was mixed with 3 parts by weight of a sulfonium salt cationic polymerization initiator "UVACURE 1590" supplied by Daicel-Cytec Co., Ltd. and 0.5 part by weight of a leveling agent "BYK-361N" supplied by BYK Chemie Co., Ltd, to prepare a curable composition. The curable composition was applied to a steel sheet using an applicator to give a coat 20 μm thick, and the obtained coat was irradiated with an ultraviolet ray to an integrated light quantity of 500 mJ/cm² using an ultraviolet irradiator (supplied by Eye Graphics Co., Ltd. under the trade name of "ECS-401GX") to cure the coat. The cured coat was post-cured at 80° C. for one hour to prepare a test piece. The test piece was attached to a rigid-body pendulum type viscoelasticity measuring instrument (supplied by A&D Co., Ltd. under the trade name of "RPT 3000") equipped with a cylindrical edge having 4 mm in diameter, and measurements were conducted at temperatures from 30° C. to 300° C. Of two or more peaks observed at different temperatures in logarithmic decrement, a peak in logarithmic decrement observed at the lowest temperature was selected, and the temperature thereof was read out, to find that the cured article had a glass transition temperature (Tg) of 136° C.

Example 5

A curable composition was prepared by mixing 100 parts by weight of the alicyclic epoxy compound prepared according to Preparation Example 2 with 3 parts by weight of a sulfonium salt cationic polymerization initiator "UVACURE 1590" supplied by Daicel-Cytec Co., Ltd. and 0.5 part by weight of a leveling agent "BYK-361N" supplied by BYK Chemie Co., Ltd. The curable composition was cured and properties of the cured article were evaluated by the procedure of Example 4, to find that the cured article had a glass transition temperature (Tg) of 135° C.

Example 6

A curable composition was prepared by mixing 100 parts by weight of the alicyclic epoxy compound prepared according to Preparation Example 3 with 3 parts by weight of a sulfonium salt cationic polymerization initiator "UVACURE 1590" supplied by Daicel-Cytec Co., Ltd. and 0.5 part by weight of a leveling agent "BYK-361N" supplied by BYK Chemie Co., Ltd. The curable composition was cured and properties of the cured article were evaluated by the procedure of Example 4, to find that the cured article had a glass transition temperature (Tg) of 122° C.

Comparative Example 2

A curable composition was prepared by mixing 100 parts by weight of the alicyclic epoxy compound prepared according to Comparative Preparation Example 1 with 3 parts by weight of a sulfonium salt cationic polymerization initiator "UVACURE 1590" supplied by Daicel-Cytec Co., Ltd. and 0.5 part by weight of a leveling agent "BYK-361N" supplied by BYK Chemie Co., Ltd. The curable composition was cured and properties of the cured article were evaluated by the procedure of Example 4, to find that the cured article had a glass transition temperature (Tg) of 113° C.

Example 7

A curable composition was prepared by mixing 100 parts by weight of the alicyclic epoxy compound prepared according to Preparation Example 1 with 158 parts by weight of a liquid alicyclic acid anhydride curing agent "Rikacid MH-700" supplied by New Japan Chemical Co., Ltd., 1 part by weight of ethylene glycol as an additive, and 0.5 part by weight of an accelerator "U-CAT 18X" supplied by SAN-APRO LIMITED. A sample was prepared by subjecting the curable composition to primary curing at 100° C. for three hours and thereafter to secondary curing at 150° C. for three hours. The glass transition temperature (Tg) of the sample cured article was measured through thermo-mechanical analysis (TMA) at a temperature elevation rate of 5° C./minute, to find that an inflection point, which indicates the glass transition temperature (Tg), was observed at 227° C. The cured article had a coefficient of linear expansion of 84 ppm, as calculated from a dimensional change from 50° C. to 200° C. determined in the above thermo-mechanical analysis. The cured article showed a transparent appearance upon heating to 300° C. at a temperature elevation rate of 5° C./minute.

Example 8

A curable composition was prepared by mixing 100 parts by weight of the alicyclic epoxy compound prepared according to Preparation Example 2 with 158 parts by weight of a liquid alicyclic acid anhydride curing agent "Rikacid MH-700" supplied by New Japan Chemical Co., Ltd., 1 part by weight of ethylene glycol as an additive, and 0.5 part by weight of an accelerator "U-CAT 18X" supplied by SAN-APRO LIMITED. The curable composition was cured and properties of the cured article were evaluated by the procedure of Example 7. The cured article was found to have a glass transition temperature (Tg) of 224° C. and a coefficient of linear expansion of 82 ppm and to show a transparent appearance upon heating to 300° C.

Example 9

A curable composition was prepared by mixing 100 parts by weight of the alicyclic epoxy compound prepared according to Preparation Example 3 with 158 parts by weight of a liquid alicyclic acid anhydride curing agent "Rikacid MH-700" supplied by New Japan Chemical Co., Ltd., 1 part by weight of ethylene glycol as an additive, and 0.5 part by weight of an accelerator "U-CAT 18X" supplied by SAN-AFRO LIMITED. The curable composition was cured and properties of the cured article were evaluated by the procedure of Example 7. The cured article was found to have a glass transition temperature (Tg) of 229° C. and a coefficient of linear expansion of 82 ppm and to show a transparent appearance upon heating to 300° C.

Comparative Example 3

A curable composition was prepared by mixing 100 parts by weight of the alicyclic epoxy compound prepared according to Comparative Preparation Example 1 with 158 parts by weight of a liquid alicyclic acid anhydride curing agent "Rikacid MH-700" supplied by New Japan Chemical Co., Ltd., 1 part by weight of ethylene glycol as an additive, and 0.5 part by weight of an accelerator "U-CAT 18X" supplied by SAN-APRO LIMITED. The curable composition was cured and properties of the cured article were evaluated by the procedure of Example 7. The cured article was found to have a glass transition temperature (Tg) of 210° C. and a coefficient of linear expansion of 83 ppm and to show a transparent appearance upon heating to 300° C.

The results are shown in Tables 1 to 4.

TABLE 1

Figure 2:
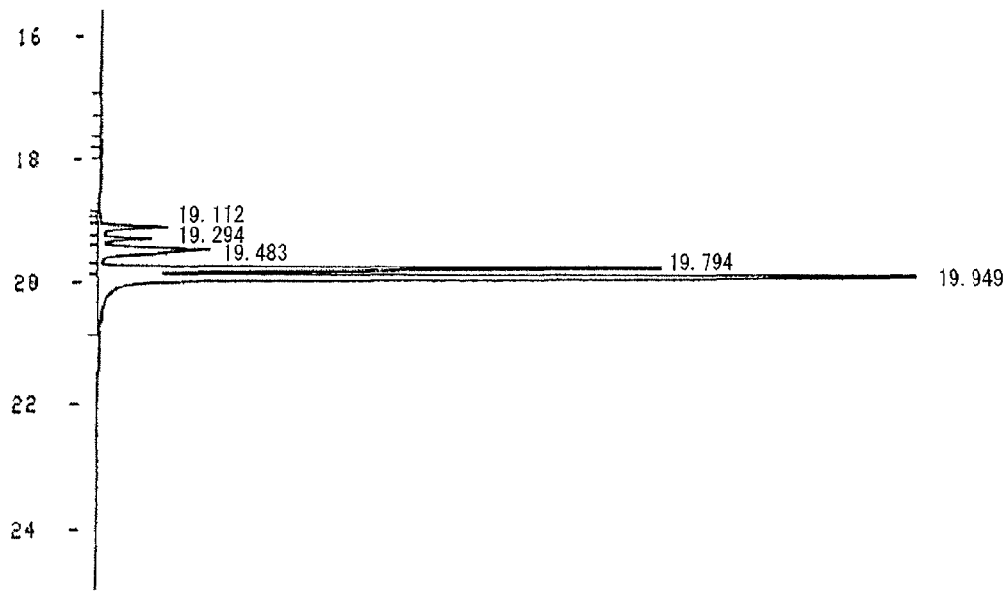
FIG. 2 depicts a gas chromatographic chart of an alicyclic diepoxy compound prepared according to Preparation Example 2.
Figure 3:
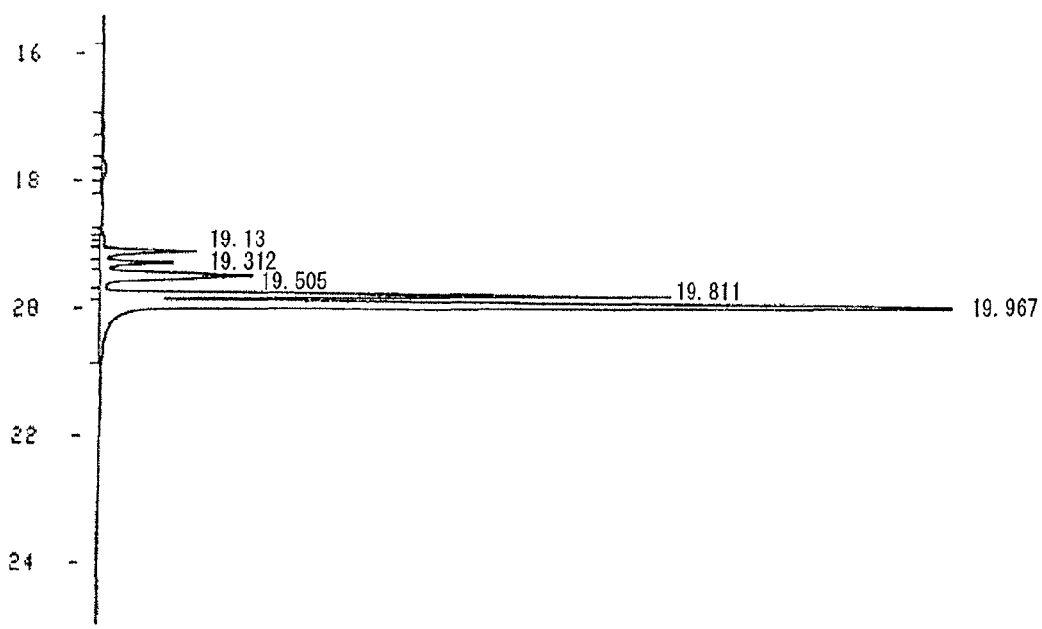
FIG. 3 depicts a gas chromatographic chart of an alicyclic diepoxy compound prepared according to Preparation Example 3.
Figure 4:
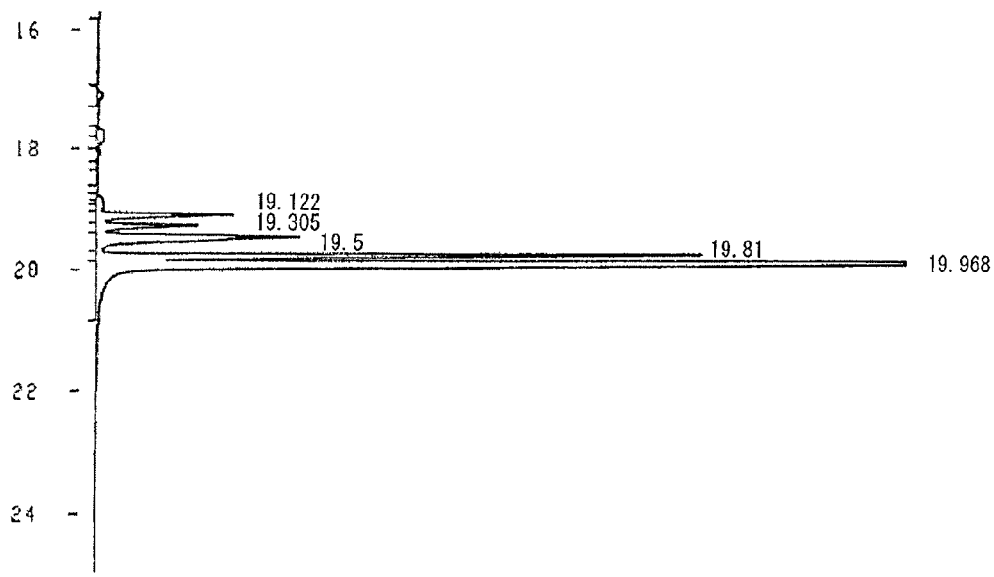
FIG. 4 depicts a gas chromatographic chart of an alicyclic diepoxy compound prepared according to Comparative Preparation Example 1.

| | | Preparation Example 1 | Preparation Example 2 | Preparation Example 3 | Comparative Preparation Example 1 |
|---|---|---|---|---|---|
| Isomer percentage | (%) | 9 | 14 | 17 | 21 |
| Oxirane-oxygen concentration | (%) | 15.0 | 15.0 | 15.0 | 14.9 |
| Viscosity | (mPa · s/25° C.) | 84 | 75 | 69 | 63 |
| GC chart | | FIG. 1 | FIG. 2 | FIG. 3 | FIG. 4 |

TABLE 2

|  |  |  | Example 1 | Example 2 | Example 3 | Comparative Example 1 |
|---|---|---|---|---|---|---|
| Curable composition | Alicyclic epoxy compound | | Prep. Ex. 1 | Prep. Ex. 2 | Prep. Ex. 3 | Com. Prep. Ex. 1 |
| | | part by weight | 100 | 100 | 100 | 100 |
| | Cationic polymerization initiator | | SAN-AID SI-60L | | | |
| | | part by weight | 0.3 | 0.3 | 0.3 | 0.3 |
| Properties of cured article | Glass transition temperature (Tg) | °C. | ≧340 | ≧340 | ≧340 | 298 |
| | Coefficient of linear expansion | ppm | 63 | 60 | 67 | 102 |
| | Appearance at 300° C. | | transparent | transparent | transparent | cloudy |

TABLE 3

|  |  |  | Example 4 | Example 5 | Example 6 | Comparative Example 2 |
|---|---|---|---|---|---|---|
| Curable composition | Alicyclic epoxy compound | | Prep. Ex. 1 | Prep. Ex. 2 | Prep. Ex. 3 | Com. Prep. Ex. 1 |
| | | part by weight | 100 | 100 | 100 | 100 |
| | Cationic polymerization initiator | | UVACURE 1590 | | | |
| | | part by weight | 3 | 3 | 3 | 3 |
| | Leveling agent | | BYK-361N | | | |
| | | part by weight | 0.5 | 0.5 | 0.5 | 0.5 |
| Properties of cured article | Glass transition temperature (Tg) | °C. | 136 | 135 | 122 | 113 |

TABLE 4

|  |  |  | Example 7 | Example 8 | Example 9 | Comparative Example 3 |
|---|---|---|---|---|---|---|
| Curable composition | Alicyclic epoxy compound | | Prep. Ex. 1 | Prep. Ex. 2 | Prep. Ex. 3 | Com. Prep. Ex. 1 |
| | | part by weight | 100 | 100 | 100 | 100 |
| | Curing agent | | Rikacid MH-700 | | | |
| | | part by weight | 158 | 158 | 158 | 158 |
| | Additive | | Ethylene glycol | | | |
| | | part by weight | 1 | 1 | 1 | 1 |
| | Accelerator | | U-CAT 18X | | | |
| | | part by weight | 0.5 | 0.5 | 0.5 | 0.5 |
| Properties of cured article | Glass transition temperature (Tg) | °C. | 227 | 224 | 229 | 210 |
| | Coefficient of linear expansion | ppm | 84 | 82 | 82 | 83 |
| | Appearance at 300° C. | | transparent | transparent | transparent | transparent |

INDUSTRIAL APPLICABILITY

Alicyclic diepoxy compounds and epoxy resin compositions according to the present invention are highly reactive upon curing, and the epoxy resin compositions give, through curing, cured articles that are superior in properties such as thermal stability. Accordingly, they are useful in a variety of fields including uses such as coatings, inks, coating materials, adhesives, sealants, encapsulants, resists, composite materials, transparent substrates, transparent sheets, transparent films, optical devices, optical lenses, optical members, insulating materials, stereo lithography, LED end-sealing materials, electronic papers, touch panels, solar cell substrates, optical waveguides, light-guiding panels, and holographic memories.

The invention claimed is:

1. An alicyclic diepoxy compound comprising a 3,4,3',4'-diepoxybicyclohexyl compound represented by following Formula (1):

[Chemical Formula 1]

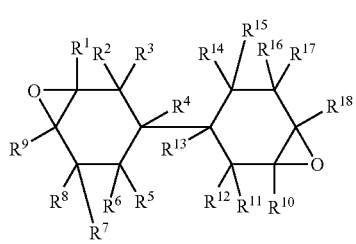

(1)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are the same as or different from one another and each represent a hydrogen atom, a halogen atom, a hydrocarbon group which may have an oxygen atom or a halogen atom, or a substituted or unsubstituted alkoxy group, wherein said alicyclic diepoxy compound contains an isomer of said 3,4,3',4'-diepoxybicyclohexyl compound as an impurity, and wherein a content of said isomer is less than 20% in terms of peak area ratio based on the total peak areas of the 3,4,3',4'-diepoxybicyclohexyl compound and the isomer, the peak areas being determined by gas chromatography.

2. An alicyclic diepoxy compound as an epoxidation product of an alicyclic diene compound, the alicyclic diene compound comprising a bicyclohexyl-3,3'-diene compound represented by following Formula (2):

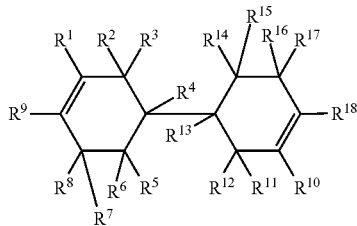

(2)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are the same as or different from one another and each represent a hydrogen atom, a halogen atom, a hydrocarbon group which may have an oxygen atom or a halogen atom, or a substituted or unsubstituted alkoxy group, wherein said bicyclohexyl-3,3'-diene compound is prepared by dehydration of a 4,4'-dihydroxybicyclohexyl compound in an organic solvent in the presence of a dehydration catalyst while distilling off by-produced water, the 4,4'-dihydroxybicyclohexyl compound being represented by following Formula (3):

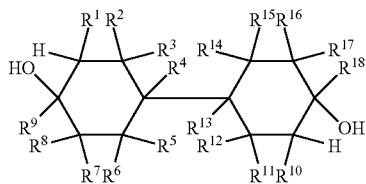

(3)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are as defined above, and wherein said alicyclic diene compound contains an isomer of said bicyclohexyl-3,3'-diene compound as an impurity, and a content of said isomer is less than 20% in terms of peak area ratio based on the total peak areas of the bicyclohexyl-3,3'-diene compound and said isomer, the peak areas being determined by gas chromatography.

3. An epoxy resin composition comprising the alicyclic diepoxy compound of claim 1 or 2.

4. The epoxy resin composition of claim 3, further comprising a curing agent and/or a curing catalyst.

5. A cured article as a cured product from the epoxy resin composition of claim 3.

6. A method of producing an alicyclic diepoxy compound including a 3,4,3',4'-diepoxybicyclohexyl compound represented by following Formula (1):

[Chemical Formula 1]

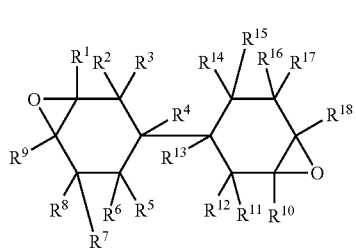

(1)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are the same as or different from one another and each represent a hydrogen atom, a halogen atom, a hydrocarbon group which may have an oxygen atom or a halogen atom, or a substituted or unsubstituted alkoxy group, wherein said alicyclic diepoxy compound may contain an isomer of said 3,4,3',4'-diepoxybicyclohexyl compound as an impurity, and wherein, when said isomer is contained in said alicyclic diepoxy compound, a content of said isomer is less than 20% in terms of peak area ratio based on the total peak areas of the 3,4,3',4'-diepoxybicyclohexyl compound and the isomer, the peak areas being determined by gas chromatography, the method comprising a step of epoxidation of an alicyclic diene compound including a bicyclohexyl-3,3'-diene compound represented by following Formula (2):

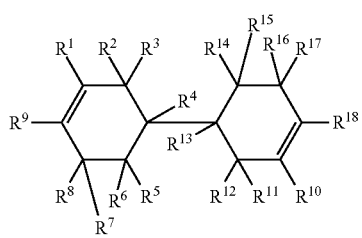

(2)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are the same as or different from one another and each represent a hydrogen atom, a halogen atom, a hydrocarbon group which may have an oxygen atom or a halogen atom, or a substituted or unsubstituted alkoxy group, wherein said bicyclohexyl-3,3'-diene compound is prepared by dehydration of a 4,4'-dihydroxybicyclohexyl compound in an organic solvent in the presence of a dehydration catalyst while distilling off by-produced water, the 4,4'-dihydroxybicyclohexyl compound being represented by following Formula (3):

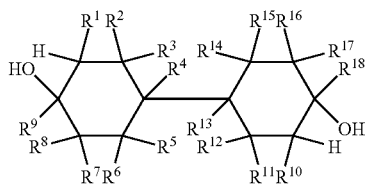 (3)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are as defined above, and wherein said alicyclic diene compound may contain an isomer of said bicyclohexyl-3,3'-diene compound as an impurity, and, when said isomer is contained in said alicyclic diene compound, a content of said isomer is less than 20% in terms of peak area ratio based on the total peak areas of the bicyclohexyl-3,3'-diene compound and said isomer, the peak areas being determined by gas chromatography.

7. An epoxy resin composition comprising the alicyclic diepoxy compound obtained by the method of claim 6,
wherein a content of an isomer of 3,4,3',4'-diepoxybicyclohexyl compound is less than 20% in terms of peak area ratio based on total peak areas of a 3,4,3',4'-diepoxybicyclohexyl compound and the isomer, the peak areas being determined by gas chromatography.

8. The epoxy resin composition of claim 7, further comprising a curing agent, a curing catalyst or a combination thereof.

9. A cured article as a cured product from the epoxy resin composition of claim 7 or 8.

* * * * *